(12) United States Patent
Zhang et al.

(10) Patent No.: US 11,426,712 B2
(45) Date of Patent: Aug. 30, 2022

(54) FISCHER-TROPSCH SYNTHESIS CATALYST CONTAINING NITRIDE SUPPORT, PREPARATION METHOD THEREFOR AND USE THEREOF

(71) Applicant: SYNFUELS CHINA TECHNOLOGY CO., LTD., Beijing (CN)

(72) Inventors: Chenghua Zhang, Beijing (CN); Yongwang Li, Beijing (CN); Yong Yang, Beijing (CN); Hulin Wang, Beijing (CN); Xianzhou Wang, Beijing (CN); Hongwei Xiang, Beijing (CN)

(73) Assignee: SYNFUELS CHINA TECHNOLOGY CO., LTD., Beijing (CN)

(*) Notice: Subject to any disclaimer, the term of this patent is extended or adjusted under 35 U.S.C. 154(b) by 0 days.

(21) Appl. No.: 16/483,893

(22) PCT Filed: Apr. 10, 2018

(86) PCT No.: PCT/CN2018/082463
§ 371 (c)(1),
(2) Date: Aug. 6, 2019

(87) PCT Pub. No.: WO2018/205787
PCT Pub. Date: Nov. 15, 2018

(65) Prior Publication Data
US 2020/0009540 A1  Jan. 9, 2020

(30) Foreign Application Priority Data

May 9, 2017 (CN) .......................... 201710320760.4

(51) Int. Cl.
*B01J 27/24* (2006.01)
*B01J 35/02* (2006.01)
(Continued)

(52) U.S. Cl.
CPC ............. *B01J 27/24* (2013.01); *B01J 23/745* (2013.01); *B01J 23/889* (2013.01);
(Continued)

(58) Field of Classification Search
CPC ............. B01J 27/24; C10G 2/33; C10G 2/331
See application file for complete search history.

(56) References Cited

U.S. PATENT DOCUMENTS 6,013,313 A * 1/2000 Nunan ................. B01J 37/0018
427/214
2005/0124706 A1* 6/2005 Wright .................... B01J 38/06
518/726

(Continued)

FOREIGN PATENT DOCUMENTS

CN     101530809 A     9/2009
CN     101663090 A     3/2010

(Continued)

OTHER PUBLICATIONS

Machine translation of CN105854919, publication date Aug. 17, 2016.*

(Continued)

*Primary Examiner* — Jun Li
(74) *Attorney, Agent, or Firm* — Nixon Peabody LLP

(57) ABSTRACT

Disclosed are a Fischer-Tropsch synthesis catalyst, a preparation method therefor and use thereof in a Fischer-Tropsch synthesis reaction. Wherein the catalyst comprises: an active component, being at least one selected from VIIIB transition metals; an optional auxiliary metal; and a nitride carrier having a high specific surface area. The catalyst is characterized in that the active metal is supported on the nitride carrier having the high specific surface, such that the active component in the catalyst is highly dispersed. The catalyst has a high hydrothermal stability, an excellent mechanical (Continued)

wear resistance, a high Fischer-Tropsch synthesis activity and an excellent high-temperature stability.

18 Claims, 3 Drawing Sheets

(51) Int. Cl.
| | |
|---|---|
| *B01J 35/10* | (2006.01) |
| *C10G 2/00* | (2006.01) |
| *B01J 23/889* | (2006.01) |
| *B01J 23/745* | (2006.01) |
| *B01J 23/89* | (2006.01) |

(52) U.S. Cl.
CPC ....... *B01J 23/8892* (2013.01); *B01J 23/8953* (2013.01); *B01J 23/8986* (2013.01); *B01J 35/023* (2013.01); *B01J 35/1014* (2013.01); *B01J 35/1019* (2013.01); *B01J 35/1061* (2013.01); *C10G 2/332* (2013.01); *C10G 2300/70* (2013.01)

(56) References Cited

U.S. PATENT DOCUMENTS

| | | | | |
|---|---|---|---|---|
| 2012/0149559 | A1* | 6/2012 | Wolan | C10G 2/331 502/319 |
| 2012/0263633 | A1* | 10/2012 | Koplin | C07C 5/00 423/213.5 |
| 2013/0274093 | A1* | 10/2013 | Woodfield | B01J 35/1061 502/177 |
| 2014/0194280 | A1* | 7/2014 | Osaki | B01J 35/006 502/330 |

FOREIGN PATENT DOCUMENTS

| | | | | |
|---|---|---|---|---|
| CN | 101767022 | A | | 7/2010 |
| CN | 101850258 | A | | 10/2010 |
| CN | 102489312 | A | * | 6/2012 ............ B01J 23/002 |
| CN | 104944391 | A | | 9/2015 |
| CN | 105195205 | A | | 12/2015 |
| CN | 105854919 | A | | 8/2016 |
| CN | 107185572 | A | | 9/2017 |
| JP | 653392 | A1 | * | 7/1995 |
| KR | 20070082696 | A | | 8/2007 |

OTHER PUBLICATIONS

Machine translation of Zhang CN101767022 A, publication date Jul. 7, 2010.*
Wu2016 (A template-free solvent-mediated synthesis of high surface area boron nitride nanosheets for aerobic oxidative desulfurization, Chem. Commun. 2016, 51 p. 144-147).*
Wang (Convenient synthesis and applications of gram scale boron nitride nanosheets, Catal. Sci. Technol. 2011, 1 p. 1119-1123).*
Zhuo et al., Machine translation of CN 104944391, published Sep. 30, 2015.*
Machine translation of CN 102489312A, publication date Jun. 2012.*
International Search Report in International Application No. PCT/CN2018/082463, dated Jun. 29, 2018 (6 pages, w/English translation).
Wu, Jianghong et al,. "Ultrathin N-rich Boron Nitride Nanosheets Supported Iron Catalyst for Fischer-Tropsch Synthesis," vol. 6, Apr. 11, 2016, RSC Advance, pp. 38356-38364 (9 pages).
Pei, Lizhai, High-Tech Ceramic Materials, "Ten-Two-Five"Teaching Materials for Materials Science and Engineering Majors in Colleges and Universities, Chapter Two: Carbide Ceramic Material, pp. 34-65, printed in Jun. 2015; and Machine translation into English.
Zhou, Wenying and Ding, Xiaowei, Thermal Polymer Material, p. 86, Printed in Apr. 2014; and Machine translation into English.
Wang, Guangzu, Superhard Material Manufacturing and Application Technology, p. 239, Printed in Sep. 2013; and Machine translation into English.
Yongde, H., "Modern Coal Chemical Technology Handbook," Chemical Industry Press (2003).
Perrichon, V. et al., "Metal dispersion of $CeO_2$-$ZrO_2$ supported platinum catalysts measured by $H_2$ or CO chemisorption,"Applied Catalysis A: General 260, pp. 1-8 (2004).
Komai, S. et al., "Determination of Metal Dispersion of Pt/$CeO_2$ Catalyst by CO-pulse Method," Journal of the Japan Petroleum Institute, 48(3): 173-177 (2005).
"Research on Foundation and Application of Coal-to-Liquid Technology: Fundamentals and Application of Coal to Oil Technologies," Shanghai Science and Technology Press, Edited by Dexiang, Z., 2013 (5 pages w/English Abstract).

* cited by examiner

FISCHER-TROPSCH SYNTHESIS CATALYST CONTAINING NITRIDE SUPPORT, PREPARATION METHOD THEREFOR AND USE THEREOF

REFERENCE TO RELATED APPLICATIONS

This application is a U.S. national stage of PCT/CN2018/082463 filed on Apr. 10, 2018, which claims the benefits of Chinese patent application. No. 201710320760.4, filed on May 9, 2017 before the China National Intellectual Property Administration, all the contents of which are incorporated herein by reference in their entireties.

TECHNICAL FIELD

The present invention belongs to the field of heterogeneous catalysis, especially Fischer-Tropsch synthesis catalysis. In particular, the present invention relates to a Fischer-Tropsch synthesis catalyst containing a novel catalyst carrier, a preparation method therefor and use thereof in Fischer-Tropsch synthesis reaction. More specifically, the present invention relates to a novel Fischer-Tropsch synthesis catalyst comprising a Group VIIIB metal supported on the carrier obtained by using a nitride as the catalyst carrier.

BACKGROUND ART

Syngas, which is a mixed gas containing CO, $H_2$, and a small amount of $CO_2$, methane and $N_2$, can be converted into hydrocarbon compounds under the action of catalysts. This reaction is referred to as the Fischer-Tropsch synthesis reaction, and the Group VIIIB transition metals, such as iron, cobalt, nickel, and ruthenium, are the active components of the catalysts commonly used in this reaction.

The Fischer-Tropsch synthesis reaction is a high temperature (150-350° C.), high pressure (10-50 bar), and strong exothermic (165 kJ/mol) reaction. One major byproduct of this reaction is water. At present, the reactors suitable for the Fischer-Tropsch synthesis reaction mainly include a fixed bed reactor, a fixed fluidized bed reactor, and a gas-liquid-solid three-phase slurry bed reactor. Therefore, the Fischer-Tropsch synthesis catalyst will undergo very harsh mechanical and chemical stresses during the reaction, which requires a very high abrasion resistance performance for the catalyst.

Some refractory oxides, such as silica, alumina, titania, zirconia and the like, are usually used as carriers of the Fischer-Tropsch synthesis catalyst. However, these carriers also bring some unavoidable disadvantages to the catalyst, such as low thermal conductivity, poor hydrothermal stability, strong surface acidity, low mechanical strength and poor abrasion resistance. Since the Fischer-Tropsch synthesis reaction is a strong exothermic reaction, the poor thermal conductivity of the catalyst may cause a retention of a large amount of reaction heat in the catalyst particles during the reaction, resulting in over-temperature of local reaction of the catalyst, poor selectivity of the target product, and more seriously resulting in losing catalytic activity by sintering the activity phase of the catalyst. Therefore, it is very important to promptly remove a large amount of reaction heat released from the inside of the catalyst particles. In addition, the high water partial pressure in the Fischer-Tropsch synthesis reaction is also very lethal to the catalyst. The literature (Journal of the Chemical Society-Chemical Communications, 1984, 10, pp. 629-630) reports that water has a very detrimental effect on alumina-supported catalysts. At a low temperature and a low water partial pressure, the alumina carrier will be partially transformed to pseudo-boehmite, which may cause the pulverization of catalysts. In order to improve the mechanical and chemical stability of Fischer-Tropsch synthesis catalysts, many researchers have tried to find new catalyst carriers with high thermal conductivity and high mass transfer efficiency.

Hexagonal boron nitride is a layered material and has been preliminarily studied as a carrier for different catalysts. For example, the literature (J. Catal., 2001, 200, pp. 1-3) reports that a Ba—Ru/BN catalyst exhibits unprecedented reactivity in the synthesis of ammonia, and no inactivation behavior is occurred during a 3500 h of reaction period. The literature (RSC Advances, 2016, 6, pp. 38356-38364) reports a hexagonal boron nitride supported iron catalyst for the Fischer-Tropsch synthesis reaction. Although the catalyst exhibits good operation stability, the phase state of iron in the catalyst is mainly metal iron with a large grain size, the degree of dispersion of Fe active phase is lower, Fischer-Tropsch synthesis reactivity is lower and methane selectivity is higher, which is disadvantage for the large-scale production of the desired hydrocarbon compounds (mainly $C_5^+$ hydrocarbons). Patent application CN 106179438A and the literature (ACS Catalysis, 2016, 6, pp. 6814-6822) report a Ni@BN/$SiO_2$ core-shell catalyst which has greater high-temperature activity and higher sintering resistance in methanation reaction than a conventional Ni/$SiO_2$ catalyst, and inhibits carbon deposition and Ni loss. However, the $SiO_2$ carrier itself has poor thermal conductivity, and therefore, the reaction heat will be retained within the catalyst particles to a certain degree, which will bring adverse effects to the reaction system. Patent CN 104591106B, as well as patent applications CN 105293453A and CN 106179443A disclose a method for preparing several hexagonal boron nitride nanosheets and a metal palladium catalyst supported by using the nanosheet as a support, which improves the dispersity of metal nanoparticles and catalytic activity in hydrogenation reaction.

Silicon nitride ($Si_3N_4$) also has trigonal phase or hexagonal phase structure (trigonal silicon nitride and hexagonal silicon nitride), which is an atomic crystal. There are a few studies on silicon nitride as a catalyst carrier. C. Méthivier et al. (Appl. Catal. A., 1999, 182, pp. 337-344) prepared silicon nitride by using CVD process, and it was used as a carrier to support palladium catalyst for using in methane oxidation reaction. Patent application WO 199920390 discloses a palladium catalyst prepared by using silicon nitride having a specific surface area of 8.8 $m^2/g$ as a carrier, using palladium acetylacetonate as a palladium source and using toluene as a solvent for methane oxidation reaction, and the above catalyst has better catalytic activity than the palladium catalyst supported on α-$Al_2O_3$. Patent CN 101767022B discloses a catalyst of Group VIII and Group IB metal supported on a silicon nitride, which is used for the decomposition of nitrous oxide. However, studies on the use of silicon nitride as a carrier for Fischer-Tropsch synthesis catalysts have not been reported so far.

In addition, currently commercial BN or $Si_3N_4$ materials have a very low specific surface area and are not suitable to be used as carriers for Fischer-Tropsch synthesis catalysts; likewise, Ni/BN catalyst (see ACS Catalysis, 2016, 6, pp. 6814-6822) or Fe/BN catalyst (see RSC Advances, 2016, 6, pp. 38356-38364) synthesized directly by chemical synthesis method has problems in severe sintering of the active phase. These fatal defects limit the use of boron nitride or silicon nitride materials in Fischer-Tropsch synthesis. Therefore, it is necessary to use a BN or $Si_3N_4$ material different from those disclosed in the prior art to exert high thermal conductivity, thereby being capable of effectively slowing down the temperature fluctuation of the catalyst bed when it is used as a Fischer-Tropsch catalyst carrier. It thus facilitates the operation of Fischer-Tropsch synthesis catalysts under more harsh reaction conditions and greatly increases the capacity of the catalyst.

SUMMARY OF THE INVENTION

The purpose of the present disclosure is to overcome the abovementioned drawbacks of the existing Fischer-Tropsch synthesis catalyst, and to provide a Fischer-Tropsch synthesis catalyst for producing hydrocarbon compounds from syngas, which is greatly improved in mass transfer and heat transfer, and therefore greatly increases the efficiency of the catalyst. The present disclosure also provides a preparation method of the catalyst and use thereof in a Fischer-Tropsch synthesis reaction. Specifically, the catalyst comprises an active phase metal such as a Group VIIIB transition metal and a boron nitride and/or silicon nitride carrier.

Thus, the present disclosure provides a Fischer-Tropsch synthesis catalyst which may comprise: an active phase metal (e.g., at least one selected from Group VIIIB transition metal iron, cobalt, nickel or ruthenium), optional auxiliary metal, and supporting the active phase metal and optional auxiliary metal on a carrier selected form boron nitride (preferably hexagonal boron nitride), silicon nitride (preferably trigonal silicon nitride, hexagonal silicon nitride) or a mixture thereof having high specific surface area. Wherein, the dispersity of the active phase metal is very high, so that the catalyst exhibits good catalyst activity. Moreover, the catalyst has excellent mass transfer and heat transfer capabilities, and can greatly improve the Fischer-Tropsch synthesis performance in a tubular fixed bed reaction.

The present disclosure further provides a method for preparing the above catalyst, comprising the following steps: (1) preparing a nitride carrier having a specific surface area of not less than 80 m$^2$/g; (2) supporting a precursor of an active metal as an active component and a precursor of an optional auxiliary metal on the nitride carrier to form a catalyst precursor; (3) molding the catalyst precursor to obtain a molded catalyst precursor; and (4) drying and calcining the molded catalyst precursor to obtain the catalyst.

The carrier of the present disclosure exhibits many beneficial properties in the preparation of Fischer-Tropsch synthesis catalysts: high thermal conductivity, high specific surface area, physicochemical abrasion resistance and high mechanical strength, and especially the high specific surface area of the carrier can promote the highly dispersion of the active phase of the catalyst and thus significantly increase the activity of the catalyst.

The present disclosure also provides use of the above Fischer-Tropsch synthesis catalyst for preparing hydrocarbon compounds by catalyzing syngas in a Fischer-Tropsch synthesis reaction. Alternatively, the present disclosure also provides a Fischer-Tropsch synthesis reaction method, wherein hydrocarbon compounds are prepared by catalyzing syngas with the Fischer-Tropsch synthesis catalyst described above. Specifically, the syngas is introduced into a Fischer-Tropsch synthesis reactor to contact with the catalyst, and the hydrocarbon compounds are prepared through carrying out a reaction by catalyzing the syngas with the catalyst.

The experimental results indicate that cobalt-based or iron-based Fischer-Tropsch synthesis catalysts obtained by using boron nitride and/or silicon nitride with high specific surface area as catalyst carriers have significantly increased catalytic activity, long-period stability and flexible operability, especially when the Fischer-Tropsch synthesis catalysts are applied to a high temperature fixed bed Fischer-Tropsch synthesis reaction. The catalyst of the present disclosure has excellent heat and mass transfer abilities, and can prepare the target hydrocarbon compounds (especially $C_5^+$ hydrocarbons, that is, hydrocarbons having 5 or more carbon atoms) with high selectivity, exhibiting excellent mechanical and chemical stabilities. Therefore, the catalyst is very suitable for the Fischer-Tropsch synthesis reaction. The catalyst is particularly suitable for Fischer-Tropsch synthesis reactions carried out in conventional fixed bed reactors or tubular reactors (with shell-and-tube heat exchanger mode) and at high space velocity.

DETAILED DESCRIPTION OF THE INVENTION

Figure 1:
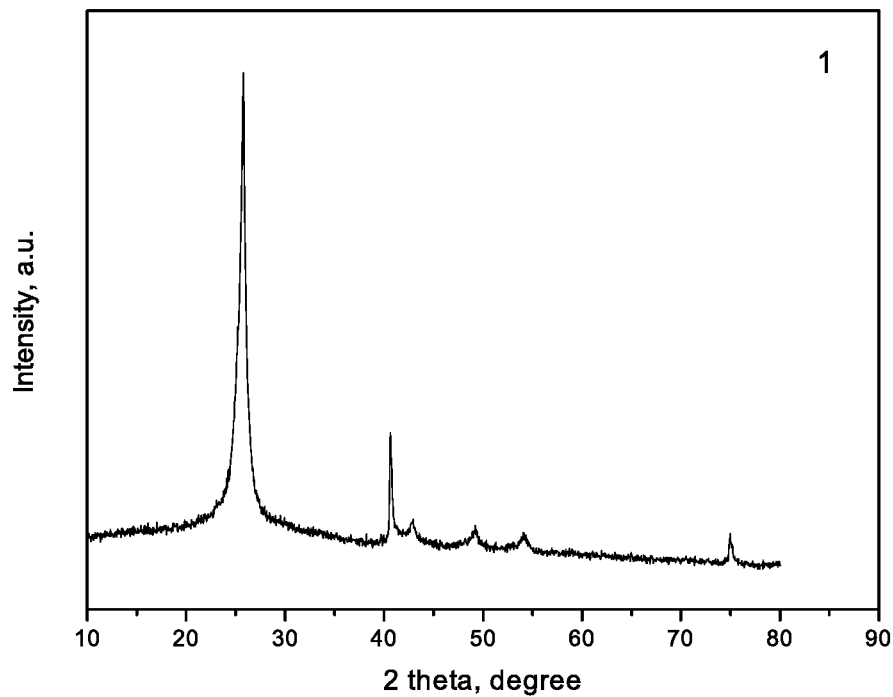
FIG. 1 is XRD pattern of the hexagonal boron nitride carrier prepared in Example 1.

As used herein, unless otherwise indicated, the term "specific surface area" means the specific surface area measured by the BET method (Brunauer-Emmet-Teller), and the measurement method is described in Standard NFX 11-621. As used herein, unless otherwise indicated, the terms "catalyst active phase", "active component", "active phase metal", "active metal" and "metal active phase" can be used interchangeably and refer to the metal component used as the active phase of the Fischer-Tropsch synthesis catalyst.

Unless otherwise indicated, all numbers representing the amounts of the components, or physicochemical properties thereof, or reaction conditions used herein should be understood as being modified by the term "about" in all instances. When the term "about" is used to describe the present invention, the term "about" denotes that an error value is present, for example, denotes a variation within a range of ±10% of a particular value.

The present invention provides a Fischer-Tropsch synthesis catalyst, wherein the catalyst comprises: an active component which is at least one selected from group VIIIB transition metals; an optional auxiliary metal; and a nitride carrier which is boron nitride, silicon nitride or a mixture thereof having a specific surface area of not less than 80 m$^2$/g; wherein the active component and the optional auxiliary metal are supported on the carrier.

Preferably, the nitride carrier can be in a nanometer size, the form of which can be nanoparticle, nanosheet, nanotube, nanocage, nanofiber, nanowire, and the like. Further, it is preferred that the nitride carrier has a specific surface area of not less than 100 m$^2$/g, preferably more than 100 m$^2$/g. More preferably, the dispersity of the active component in the Fischer-Tropsch synthesis catalyst is from 15% to 75%, so that the catalyst has a better catalytic activity. The boron nitride is preferably a hexagonal boron nitride. The silicon nitride is preferably a trigonal silicon nitride and/or a hexagonal silicon nitride.

The active component (i.e., the active phase metal) is preferably at least one selected from iron, cobalt, nickel, and ruthenium. The auxiliary metal is at least one selected from manganese (Mn), chromium (Cr), zinc (Zn), molybdenum (Mo), copper (Cu), platinum (Pt), palladium (Pd), rhodium (Rh), iridium (Ir), gold (Au), silver (Ag), magnesium (Mg), calcium (Ca), strontium (Sr), barium (Ba), sodium (Na) and potassium (K).

The mass ratio of the active phase metal to the carrier is (0.1-400):100. When the active phase metal is selected from iron, cobalt and/or nickel, the mass ratio of the active phase metal to the carrier is (1-400):100, preferably (5-100):100, more preferably (10-80):100, most preferably (20-50):100, particularly preferably (30-40):100. When the active phase metal is selected from ruthenium, the mass ratio of the active phase metal to the carrier is (0.1-10):100, preferably (0.5-8):100, more preferably (1-6):100, most preferably (3-5):100.

The mass ratio of the auxiliary metal to the carrier is (2000 ppm-60):100. In particular, when the auxiliary metal is selected from manganese, chromium, molybdenum and/or zinc, the mass ratio of the auxiliary metal to the carrier is (1-40):100, preferably (5-30):100, more preferably (10-20):100, most preferably (15-20):100. When the auxiliary metal is selected from copper, the mass ratio of the auxiliary metal to the carrier is (0.5-15):100, preferably (1-10):100, more preferably (2-6):100. When the auxiliary metal is selected from platinum, palladium, rhodium, iridium, silver, and/or gold, the mass ratio of the auxiliary metal to the carrier is (0.002-1):100, preferably (0.01-0.5):100, more preferably (0.05-0.3):100, most preferably (0.1-0.2):100. When the auxiliary metal is selected from magnesium, calcium, strontium, barium, sodium and/or potassium, the mass ratio of the auxiliary metal to the carrier is (0.5-15):100, preferably (1-12):100, more preferably (2-9):100.

Preferably, the mass ratio of active component:auxiliary metal:carrier in the catalyst is (0.1-300):(0.002-30):100.

The present disclosure also provides a method for preparing the above catalyst, wherein the method comprises the following steps: (1) preparing a nitride carrier having a specific surface area of not less than 80 m$^2$/g; (2) supporting a precursor of active metal as an active component and a precursor of optional auxiliary metal on the nitride carrier to form a catalyst precursor; (3) molding the catalyst precursor to obtain a molded catalyst precursor; and (4) drying and calcining the molded catalyst precursor to obtain the catalyst.

Preferably, in the above step (1), the nitride carrier is a boron nitride (preferably hexagonal boron nitride) carrier and/or a silicon nitride (preferably trigonal silicon nitride, hexagonal silicon nitride) carrier. Preferably, the nitride carrier of the present invention can be prepared by a thermochemical synthesis method or a mechanical method.

Wherein, a boron nitride carrier (including hexagonal boron nitride) can be prepared by a thermochemical synthesis method, involving a thermochemical reaction of the mixture of a boron precursor, a nitrogen precursor and a transition metal compound in an inert atmosphere. More specifically, the method comprises the following steps: (a) reacting a mixture of a boron precursor, a nitrogen precursor, and a transition metal compound under an inert atmosphere in a closed autoclave or a pressurized reactor, to give a crude product containing boron nitride; (b) filtering and washing the crude product containing boron nitride obtained in step (a) with mineral acid and polar solvent, respectively, to give boron nitride powder; (c) drying and calcining the boron nitride powder to give the boron nitride carrier.

The silicon nitride carrier can be prepared by the following thermochemical synthesis method, involving a high temperature liquid phase reaction of a mixture of a silicon precursor, a nitrogen precursor, and solvents. More specifically, the method comprises the following steps: (a') reacting a mixture of a silicon precursor and a nitrogen precursor in a sealed autoclave in the presence of an organic solvent, to give a crude product containing silicon nitride; (b') leaching the crude product containing silicon nitride obtained in step (a') with a mineral acid, to give an acid-leached crude product containing silicon nitride; (c') washing the acid-leached crude product containing silicon nitride with deionized water and solvent respectively and filtering, to give silicon nitride powder; (d') drying and calcining the silicon nitride powder to obtain the silicon nitride carrier.

The boron precursor may be selected from, but not limited to, boron oxide ($B_2O_3$), sodium borate ($Na_2B_4O_7$), sodium borohydride ($NaBH_4$), boric acid ($H_3BO_3$), borane, borazine ($H_6B_3N_3$), or any mixture thereof. The silicon precursor may be selected from, but not limited to, silicon tetrachloride, tetraethyl orthosilicate, methyl orthosilicate, silane, silane coupling agent, silaimines, or any mixture thereof. The nitrogen precursor may be selected from, but not limited to, sodium azide, sodium amide, polycyanamide, guanidine, urea, ammonia, borazine, ammonium chloride or any mixture thereof. The inert atmosphere may be, but not limited to, a nitrogen atmosphere, an argon atmosphere, a helium atmosphere, or any mixed atmosphere thereof. The transition metal compound may be selected from, but not limited to, $Fe_2O_3$, $Fe_3O_4$, anhydrous $FeCl_3$, $Co_2O_3$, $Co_3O_4$, CoO, anhydrous $CoCl_2$, NiO, or any mixture thereof. The polar solvent in step (b) may be selected from, but not limited to, water, methanol, ethanol, propanol, tetrahydrofuran, dimethylformamide or any mixture thereof.

The boron precursor, the nitrogen precursor, and the transition metal compound may be mixed by mechanical mixing to form a mixture, wherein the atomic ratio of nitrogen to boron is from 2:1 to 6:1, preferably from 3:1 to 5:1, most preferably from 3.5:1 to 4.5:1. The atomic ratio of transition metal to boron may be, for example, from 0.02:1 to 0.5:1.

In step (a), a mixture of a boron precursor, a nitrogen precursor and a transition metal compound may be reacted under the following conditions: a temperature is from 400° C. to 1100° C., preferably from 600° C. to 1000° C., most preferably from 800° C. to 900° C.; a preferred pressure is from 0.2 MPa to 10 MPa, preferably from 0.5 MPa to 5 MPa. Further preferably, the reaction time is from 1 h to 20 h, preferably from 10 h to 12 h. The mineral acid may be selected from, but not limited to, hydrochloric acid, sulfuric acid, and nitric acid. The concentration of the mineral acid is from 0.1 to 5 mol/L, preferably from 0.5 to 2.5 mol/L, most preferably from 1.0 to 1.5 mol/L.

The organic solvent in step (a') may be selected from, but not limited to, benzene, toluene, xylene, ethylbenzene, hexane, heptane, octane, decane, liquid paraffin, trioctylamine or any mixture thereof. In the mixture of the silicon precursor and the nitrogen precursor in step (a'), the atomic ratio of nitrogen to silicon is (0.01-10):1, preferably (0.1-5):1, most preferably (0.2-1):1. The volume ratio of the organic solvent to the silicon precursor in step (a') is (0.1-10):1, preferably (0.5-5):1, most preferably (1-2):1. In step (a'), a mixture of the silicon precursor and the nitrogen precursor may be reacted under the following conditions: a temperature is from 300° C. to 600° C., preferably from 400° C. to 500° C.; a preferred pressure is from 0.2 MPa to 10 MPa, preferably from 0.5 MPa to 5 MPa.

Further preferably, the reaction time is from 1 h to 20 h, preferably from 5 h to 10 h. In step (c'), the solvent may be selected from, but not limited to, methanol, ethanol, propanol, tetrahydrofuran, dimethylformamide or any mixture thereof.

The boron nitride powder or silicon nitride powder can be dried and calcined in air, in an inert atmosphere or in vacuum. The drying temperature may be from 20° C. to 150° C., preferably from 80° C. to 150° C.; preferably the drying duration may be from 1 h to 24 h, preferably from 8 h to 12 h. The calcining temperature may be from 250° C. to 650° C., preferably from 350° C. to 600° C., most preferably from 450° C. to 550° C.; preferably the calcining duration may be, for example, from 1 h to 6 h.

As an exemplary embodiment, the boron nitride and silicon nitride carriers of the present disclosure may also be prepared by a mechanical method, which involves crushing the ordinary boron nitride and silicon nitride with low specific surface area by ball milling, ultrasound and the like, to give a boron nitride or silicon nitride carrier having a specific surface area of 80 $m^2/g$ or more. For example, the hexagonal boron nitride, or the trigonal or hexagonal silicon nitride carrier of the present disclosure can be prepared from commercially available hexagonal boron nitride, trigonal silicon nitride, or hexagonal silicon nitride by grinding the same through a mechanical method (e.g., ball milling) to a specific surface area of 80 $m^2/g$ or more.

As a preferred example, in the above step (2), the precursor of the active metal and the precursor of the auxiliary metal may be supported on the nitride carrier by impregnation, co-precipitation, water/solvent thermal synthesis, chemical vapor deposition, and/or atomic layer deposition and the like.

As an example of the impregnation method, the precursor of the active metal and the precursor of the auxiliary metal may be supported on the nitride carrier by co-impregnation or step-by-step impregnation method at any temperature, for example, room temperature (e.g., 15° C. to 40° C.). Wherein, an exemplary co-impregnation method comprises mixing the precursor of the active metal and the precursor of the auxiliary metal according to their composition proportion in the catalyst and dissolving in a solvent to form an impregnation solution, and then impregnating the impregnation solution on the nitride carrier. An exemplary step-by-step impregnation method includes dissolving the precursor of the active metal and the precursor of the auxiliary metal in solvents, respectively, to form separate impregnation solutions, and then impregnating the same on the nitride carrier step by step. Wherein, the impregnation may be an isometric impregnation or an excessive impregnation. An isometric impregnation means that the volume of the impregnation solution is equal to the pore volume of the carrier; an excessive impregnation means that the volume of the impregnation solution is greater than the pore volume of the carrier. For example, the active metal and the auxiliary metal can be supported on the nitride carrier by co-impregnating or stepwise impregnating the hexagonal boron nitride, the trigonal silicon nitride, the hexagonal silicon nitride or a mixture thereof with the impregnation solution formed by the precursor of the active metal and the precursor of the auxiliary metal.

The solvent forming the impregnation solution may be water, methanol, methylamine, dim ethylamine, N,N-dimethylformamide, N-methylformamide, formamide, ethanol, ethylene glycol, diethyl ether, ethylamine, acetonitrile, acetamide, propanol, acetone, propionitrile, tetrahydrofuran, dioxane, butanol, pyridine, morpholine, quinoline, toluene, xylene, heptane or any mixture thereof, but not limited thereto.

Alternatively, the precursor of the active metal and the precursor of the auxiliary metal can be converted to hydrated hydroxide and oxide forms by a co-precipitation method, to be deposited on the nitride carrier. Wherein, an exemplary co-precipitation method comprises mixing the precursor of the active metal and the precursor of the auxiliary metal according to their composition proportion in the catalyst and dissolving in a solvent to form a mixed salt solution; mixing the mixed salt solution with a nitride carrier powder according to their composition proportion in the catalyst and stirring to form a uniformly dispersed suspension; mixing the suspension with an alkaline precipitant solution, precipitating, standing still, filtering, and washing to give a catalyst precursor. For example, the active metal and the auxiliary metal can be supported on the nitride carrier by forming a suspension with the mixed salt solution and the hexagonal boron nitride, trigonal silicon nitride, hexagonal silicon nitride or a mixture thereof, and then co-precipitating the same with an alkaline precipitant solution.

The alkaline precipitant solution may be an alkali metal hydroxide solution, such as an aqueous solution of sodium hydroxide and/or potassium hydroxide; or an alkali metal carbonate or bicarbonate solution such as an aqueous solution of sodium carbonate, sodium bicarbonate, potassium carbonate and/or potassium bicarbonate; or an aqueous solution of ammonia, an aqueous solution of ammonium carbonate or an aqueous solution of ammonium bicarbonate, preferably an aqueous solution of ammonia.

Alternatively, the precursor of the active metal and the precursor of the auxiliary metal may be converted to a metal, a hydrated metal hydroxide, a hydrated metal oxide or the like by a water/solvent thermal synthesis method, to be deposited on the nitride carrier. For example, the active metal and the auxiliary metal can be supported on the nitride carrier by forming a mixed solution from the precursor of the active metal and the precursor of the auxiliary metal with the hexagonal boron nitride, trigonal silicon nitride, hexagonal silicon nitride or a mixture thereof in a solvent, and carrying out the water/solvent thermal synthesis.

The solvent forming the above mixed salt solution or alkali metal hydroxide solution or alkali metal carbonate solution or alkali metal bicarbonate solution, and the solvent used in the water/solvent thermal synthesis method may be water, methanol, methylamine, dimethylamine, N,N-dimethylformamide, N-methylformamide, formamide, ethanol, ethylene glycol, ethylamine, acetonitrile, acetamide, propanol, propionitrile, tetrahydrofuran, dioxane, butanol, pyridine, morpholine, quinoline or any mixture thereof, but not limited thereto.

Alternatively, the precursor of the active metal and the precursor of the auxiliary metal may be converted to a metal, a metal carbide, a metal nitride, a metal oxide or the like by a chemical vapor deposition method, to be deposited on the nitride carrier. For example, the active metal and the auxiliary metal can be deposited on the hexagonal boron nitride, the trigonal silicon nitride, the hexagonal silicon nitride or a mixture thereof as a carrier by heating an organometallic compound containing the active metal and the auxiliary metal under high vacuum ($10^{-1}$ Pa to $10^{-6}$ Pa) or atmospheric pressure (i.e., one atmosphere) and undergoing a chemical vapor deposition.

Alternatively, the precursor of the active metal and the precursor of the auxiliary metal may be converted to a metal, a metal carbide, a metal nitride, a metal oxide or the like by an atomic layer deposition method, to be deposited on the nitride carrier. For example, the active metal and the auxiliary metal can be deposited on the hexagonal boron nitride, trigonal silicon nitride, hexagonal silicon nitride or a mixture thereof as a carrier via the atomic layer deposition method by alternately adsorbing an oxidizing agent and a gas compound containing the active metal and the auxiliary metal in a high vacuum ($10^{-1}$ Pa to $10^{-6}$ Pa) chamber.

The precursor of the active metal is one or more selected from ferric nitrate (preferably ferric nitrate nonahydrate), ferric chloride (preferably ferric chloride hexahydrate), ferrous chloride, ferrous sulfate, ferrous acetate, iron(III) acetylacetonate, carbonyl iron, ferrocene, cobalt nitrate (preferably cobalt nitrate hexahydrate), cobalt chloride (preferably cobalt chloride hexahydrate), cobalt formate, cobalt acetate, cobalt acetylacetonate, cobalt carbonyl, nickel nitrate, nickel chloride, nickel sulfate, nickel acetate, nickel acetylacetonate, nickel carbonyl, ruthenium chloride, ruthenium nitrate, triphenylphosphine chlorocarbonylruthenium, carbonyl ruthenium chloride, ammonium chlororuthenate, ruthenium nitrosyl nitrate, but not limited thereto.

The precursor of the auxiliary metal is one or more selected from manganese nitrate, manganese chloride, manganese acetate, manganese acetylacetonate, manganese carbonyl, zinc nitrate, zinc chloride, zinc sulfate, zinc acetate, zinc acetylacetonate, chromium nitrate, chromium chloride, chromium sulfate, ammonium molybdate (preferably ammonium heptamolybdate), platinum chloride, platinum nitrate, chloroplatinic acid, ammonium chloroplatinate, diammine platinum nitrite, rhodium nitrate, rhodium chloride, rhodium sulfate, rhodium acetate, tris(triphenylphosphine) rhodium chloride, acetylacetonatocarbonyltriphenylphosphinerhodium, palladium nitrate, palladium chloride, palladium sulfate, palladium acetate, ammonium tetrachloropalladate, ammonium hexachloropalladate, triphenylphosphine palladium, chloroiridic acid, iridium chloride, iridium acetate, ammonium chloroiridate, gold chloride, chloroauric acid, ammonium chloroaurate, silver nitrate, silver acetate, silver carbonate, magnesium nitrate, magnesium chloride, magnesium acetate, calcium nitrate, calcium chloride, calcium acetate, strontium nitrate, strontium chloride, strontium acetate, sodium nitrate, sodium chloride, sodium acetate, sodium hydroxide, sodium carbonate, sodium bicarbonate, potassium nitrate, potassium chloride, potassium hydroxide, potassium carbonate, potassium bicarbonate, potassium acetate, but not limited thereto.

The catalyst precursor in step (2) may be dried, calcined or the like before step (3).

As a preferred example, in the above step (3), the catalyst precursor may be molded by a molding method selected from spray drying, compression molding, rotational molding, extrusion molding, or molding in oil. Preferably, the molded catalyst precursor may be in a form of particles, microspheres, sheets, strips, columns, rings, porous sheets, and clover shapes.

As a preferred example, in the above step (4), drying of the molded catalyst precursor may be carried out in air, in an inert atmosphere or in vacuum. The preferred drying temperature is from 20° C. to 150° C., preferably from 80° C. to 150° C. The preferred drying duration is from 1 h to 24 h, preferably from 8 h to 12 h. In certain examples, the molded catalyst precursor can be dried twice or more. Further preferably, the molded catalyst precursor can be calcined in an inert atmosphere or an oxidizing atmosphere.

The preferred calcination temperature is from 250° C. to 650° C., preferably from 350° C. to 600° C., most preferably from 450° C. to 550° C. The preferred calcination duration can be from 1 h to 6 h. For example, the molded catalyst precursor can be calcined twice or more.

The present disclosure also relates to use of the above catalyst for preparing hydrocarbon compounds by catalyzing syngas in a Fischer-Tropsch synthesis reaction. Alternatively, the present disclosure also relates to a Fischer-Tropsch synthesis reaction method, wherein hydrocarbon compounds are prepared through carrying out a Fischer-Tropsch synthesis reaction by catalyzing syngas with the above Fischer-Tropsch synthesis catalyst.

As a preferred example, the catalyst is previously reduced in a reducing atmosphere prior to application of the catalyst of the present invention to a Fischer-Tropsch synthesis reaction. The reducing atmosphere may be a pure hydrogen atmosphere, a CO atmosphere, a syngas atmosphere, an ammonia gas atmosphere, a diluted hydrogen atmosphere, a diluted CO atmosphere, a diluted syngas atmosphere, and a diluted ammonia gas atmosphere. The volume ratio of $H_2$ to CO in the syngas is from 0.01:1 to 1000:1. Each of the diluted reducing atmosphere may further contain nitrogen, argon, helium, $CO_2$ and $CH_4$ in addition to the corresponding reducing atmospheres, and preferably the volume concentration of the reducing gas in each of the diluted atmospheres is greater than 10%, preferably greater than 25%, more preferably 50%, most preferably 75%, and most preferably greater than 90%. The Fischer-Tropsch synthesis catalyst is subjected to a further reduction treatment to form a reduced state Fischer-Tropsch synthesis catalyst having a certain degree of reduction (i.e., a percentage of a metal phase, a metal carbide, and a metal nitride relative to total active phase metal). Preferably, the reduced-state Fischer-Tropsch synthesis catalyst has a degree of reduction of at least greater than 60%, preferably greater than 75%, and most preferably greater than 85%. Further, the metal content in the catalyst precursor or the catalyst can be measured by a known conventional elemental analysis method, such as ICP-AES, X-ray fluorescence spectroscopy or the like.

The degree of reduction of the catalyst can be determined by a known temperature-programmed method, taking the measurement for the degree of reduction of the cobalt-based catalyst as example: (1) the temperature of the catalyst sample is stably raised to a reduction temperature (400° C.) at a rate of 10° C./min in 10% $H_2$, and maintained for 6 h, $H_2$ consumption curve is determined by TCD or MS detector, labeled as TPR1; (2) after the end of the reduction process, without cooling down, the sample is steadily heated to 1000° C. at a rate of 10° C./min in the same reducing atmosphere and kept for 10 min, to obtain $H_2$ consumption curve TPR2; (3) TPR1 and TPR2 are respectively integrated to obtain the $H_2$ consumption of the two curves, and TPR1/(TPR1+TPR2) is the reduction degree of the catalyst (expressed as a percentage). After the end of reduction, since the active metal in the catalyst is active to oxygen in air, the catalyst can be sealed and stored in a waxy heavy hydrocarbon (i.e., a saturated linear alkane having a carbon number of 18 or higher and a mixture thereof) or transferred to a Fischer-Tropsch synthesis reactor.

The volume ratio of $H_2$ to CO in the syngas of the Fischer-Tropsch synthesis reaction is from 0.5:1 to 3.0:1, preferably from 1.0:1 to 2.5:1, more preferably from 1.2:1 to 2.2:1, most preferably from 1.5:1 to 2.0:1. The Fischer-Tropsch synthesis reaction can be carried out in a continuous reaction process or a batch reaction process. The Fischer-Tropsch synthesis reaction can be carried out by using one or more fixed bed reactors, microchannel reactors, continuous stirred slurry bed tank reactors, jet circulation reactors, slurry bubble column reactors or fluidized bed reactors. A pressure of the Fischer-Tropsch synthesis reaction is from 1.0 MPa to 6.0 MPa, and a temperature thereof is from 120° C. to 350° C. When the Fischer-Tropsch synthesis reaction is carried out in a continuous reaction process, the reaction space velocity is from 100 to 60,000 NL/Kg/h.

For example, when the Fischer-Tropsch synthesis catalyst is a cobalt catalyst, the volume ratio of $H_2$ to CO in the syngas is from 1.0:1 to 3.0:1, preferably from 1.5:1 to 2.5:1, most preferably from 1.8:1 to 2.2:1. The preferred pressure of the Fischer-Tropsch synthesis reaction is from 1.0 MPa to 6.0 MPa, preferably from 1.5 MPa to 4.5 MPa, and most preferably from 2.0 MPa to 3.0 MPa. The preferred temperature of the Fischer-Tropsch synthesis reaction is from 150° C. to 280° C., preferably from 180° C. to 260° C., most preferably from 200° C. to 240° C. When the Fischer-Tropsch synthesis reaction is carried out in a continuous reaction process, the reaction space velocity is from 100 to 25,000 NL/kg/h, preferably from 1,000 to 20,000 NL/kg/h, most preferably from 5,000 to 10,000 NL/kg/h. Alternatively, for example, when the Fischer-Tropsch synthesis catalyst is an iron catalyst, the volume ratio of $H_2$ to CO in the syngas is from 0.5:1 to 3.0:1, preferably from 1.0:1 to 2.5:1, more preferably from 1.2:1 to 2.2:1, most preferably from 1.5:1 to 2.0:1. The preferred pressure of the Fischer-Tropsch synthesis reaction is from 1.0 MPa to 6.0 MPa, preferably from 1.5 MPa to 5.5 MPa, more preferably from 2.0 MPa to 5.0 MPa, most preferably from 2.5 MPa to 4.0 MPa. The preferred temperature of the Fischer-Tropsch synthesis reaction is from 220° C. to 350° C., preferably from 240° C. to 330° C., most preferably from 260° C. to 300° C. When the Fischer-Tropsch synthesis reaction is carried out in a continuous reaction process, the reaction space velocity is from 100 to 60,000 NL/kg/h, preferably from 1,000 to 40,000 NL/kg/h, and most preferably from 10,000 to 20,000 NL/kg/h.

The exemplary embodiment described in the present disclosure has the following features: simple preparation method of the catalyst, low cost of raw materials, low production cost, and good repeatability; and the catalyst of the present disclosure has a large specific surface area (not less than 80 m$^2$/g), an ultrahigh active metal dispersity (15%-75%), higher mechanical strength (wear index of 1-2.0%·h$^{-1}$), higher thermal stability and good anti-sintering ability of metal active phase. When the catalyst of the present disclosure is applied to a Fischer-Tropsch synthesis reaction, it has better syngas conversion activity, hydrocarbon compound selectivity and high temperature stability, compared with the catalyst prepared by direct chemical synthesis or a catalyst comprising conventional carrier ($SiO_2$ or $Al_2O_3$).

For example, when used at a reaction temperature of from 230° C. to 250° C. and a reaction space velocity of 10000 NL/Kg/h, the cobalt-based catalyst comprising boron nitride or silicon nitride carrier of the present disclosure can achieves maintaining the conversion rate of CO at 10% or more, greater than 85% of the selectivity of $C_5^+$ hydrocarbons and less than 8% of the selectivity of methane. The CO conversion was tested for stable operation over 100 h or more: the initial reaction temperature was 220° C. and the intensive test temperature was 250° C. The conversion stability of the catalyst is maintained at 0.8 or more, and even greater than 0.9. For another example, when used at a reaction temperature of from 280° C. to 320° C. and a reaction space velocity of 15000 NL/Kg/h or more, the iron-based catalyst comprising a boron nitride or silicon nitride carrier of the present disclosure achieves maintaining the conversion of CO at 10% or more, less than 10% (or even less than 5%) of the selectivity of $CO_2$, greater than 90% of the selectivity of $C_5^+$ hydrocarbons and less than 5% of the selectivity of methane. The CO conversion was tested for stable operation over 100 h or more: the initial reaction temperature was 280° C. and the intensive test temperature was 300° C. The conversion stability of the catalyst is maintained at 0.8 or more, and even greater than 0.9.

As used herein, unless otherwise indicated, the term "conversion stability" is defined as the quotient obtained from the initial conversion rate of CO at an initial lower temperature (initial reaction temperature) being divided by the final conversion rate resulted from the catalyst, which has undergone a higher reaction temperature (intensive test temperature) over a period of time, at the initial reaction temperature; i.e., the quotient or percentage of dividing the final activity by the initial activity.

The content of the present invention can be exemplarily illustrated by the description in the following numbered paragraphs:

1. A Fischer-Tropsch synthesis catalyst, wherein the catalyst comprises: an active component, which is at least one selected from group VIIIB transition metals; an optional auxiliary metal; and a nitride carrier, which is boron nitride, silicon nitride or a mixture thereof having a specific surface area of not less than 80 m$^2$/g; wherein the active component and the optional auxiliary metal are supported on the carrier.

2. The catalyst according to paragraph 1, wherein a dispersity of the active component is from 15% to 75%.

3. The catalyst according to paragraph 1 or 2, wherein the active component is at least one selected from iron, cobalt, nickel and ruthenium.

4. The catalyst according to any one of paragraphs 1 to 3, wherein the auxiliary metal is at least one selected from the group comprising manganese, chromium, zinc, molybdenum, copper, platinum, palladium, rhodium, iridium, gold, silver, magnesium, calcium, strontium, barium, sodium and potassium.

5. The catalyst according to any one of paragraphs 1 to 4, wherein the carrier has a specific surface area of not less than 100 m$^2$/g, preferably more than 100 m$^2$/g.

6. The catalyst according to any one of paragraphs 1 to 5, wherein the boron nitride is a hexagonal boron nitride.

7. The catalyst according to any one of paragraphs 1 to 6, wherein the silicon nitride is a trigonal silicon nitride and/or a hexagonal silicon nitride.

8. The catalyst according to any one of paragraphs 1 to 7, wherein a form of the carrier is a nanoparticle, a nanosheet, a nanotube, a nanocage, a nanofiber, and/or a nanowire.

9. The catalyst according to any one of paragraphs 1 to 8, wherein a mass ratio of the active component to the carrier is (0.1-400):100.

10. The catalyst according to any one of paragraphs 1 to 9, wherein the active component is at least one selected from iron, cobalt and nickel, and the mass ratio of the active component to the carrier is (1-400):100, preferably (5-100):100, more preferably (10-80):100, most preferably (20-50):100, particularly preferably (30-40):100.

11. The catalyst according to any one of paragraphs 1 to 9, wherein the active component is ruthenium, and the mass ratio of the active component to the carrier is (0.1-10):100, preferably (0.5-8):100, more preferably (1-6):100, most preferably (3-5):100.

12. The catalyst according to any one of paragraphs 1 to 11, wherein a mass ratio of the auxiliary metal to the carrier is (2000 ppm-60):100.

13. The catalyst according to any one of paragraphs 1 to 12, wherein the auxiliary metal is at least one selected from manganese, chromium, molybdenum and zinc, and the mass ratio of the auxiliary metal to the carrier is (1-40):100, preferably (5-30):100, more preferably (10-20):100, most preferably (15-20):100.

14. The catalyst according to any one of paragraphs 1 to 12, wherein the auxiliary metal is copper, and the mass ratio of the auxiliary metal to the carrier is (0.5-15):100, preferably (1-10):100, more preferably (2-6):100.

15. The catalyst according to any one of paragraphs 1 to 12, wherein the auxiliary metal is at least one selected from platinum, palladium, rhodium, iridium, silver and gold, and the mass ratio of the auxiliary metal to the carrier is (0.002-1):100, preferably (0.01-0.5):100, more preferably (0.05-0.3):100, most preferably (0.1-0.2):100.

16. The catalyst according to any one of paragraphs 1 to 12, wherein the auxiliary metal is at least one selected from magnesium, calcium, strontium, barium, sodium and potassium, and the mass ratio of the auxiliary metal to the carrier is (0.5-15):100, preferably (1-12):100, more preferably (2-9):100.

17. The catalyst according to any one of paragraphs 1 to 9 and 12, wherein a mass ratio of the active metal:the auxiliary metal:the carrier is (0.1-300):(0.002-30):100.

18. A method for preparing the Fischer-Tropsch synthesis catalyst according to any one of paragraphs 1-17, wherein the method comprises the following steps: (1) preparing a nitride carrier having a specific surface area of not less than 80 $m^2/g$; (2) supporting a precursor of active metal as an active component and a precursor of optional auxiliary metal on the nitride carrier to form a catalyst precursor; (3) molding the catalyst precursor to obtain a molded catalyst precursor; and (4) drying and calcining the molded catalyst precursor to obtain the catalyst.

19. The method according to paragraph 18, wherein the nitride carrier is a boron nitride carrier and/or a silicon nitride carrier.

20. The method according to paragraph 18 or 19, wherein the nitride carrier is a hexagonal boron nitride carrier and/or a trigonal silicon nitride or a hexagonal silicon nitride carrier.

21. The method according to any one of paragraphs 18 to 20, in step (1), the nitride carrier is prepared by a mechanical method or a thermochemical synthesis method.

22. The method according to paragraph 21, wherein the nitride carrier is a boron nitride carrier, which is prepared by a thermochemical synthesis method comprising the following steps: (a) reacting a mixture of a boron precursor, a nitrogen precursor and a transition metal compound under an inert atmosphere in a closed autoclave or a pressurized reactor, to give a crude product containing boron nitride; (b) filtering and washing the crude product containing boron nitride obtained in step (a) with a mineral acid and polar solvent, respectively, to give boron nitride powder; (c) drying and calcining the boron nitride powder to give the boron nitride carrier.

23. The method according to paragraph 22, wherein the boron precursor is selected from boron oxide, sodium borate, sodium borohydride, boric acid, borane, borazine or any mixture thereof.

24. The method according to paragraph 22 or 23, wherein the transition metal compound is selected from $Fe_2O_3$, $Fe_3O_4$, anhydrous $FeCl_3$, $Co_2O_3$, $Co_3O_4$, CoO, anhydrous $CoCl_2$, NiO, or any mixture thereof.

25. The method according to any one of paragraphs 22 to 24, wherein the inert atmosphere can be a nitrogen atmosphere, an argon atmosphere, a helium atmosphere, or any mixed atmosphere thereof.

26. The method according to any one of paragraphs 22 to 25, wherein the boron precursor, the nitrogen precursor, and the transition metal compound are mixed by mechanical mixing to form the mixture.

27. The method according to any one of paragraphs 22 to 26, in step (a), an atomic ratio of nitrogen to boron in the mixture is from 2:1 to 6:1, preferably from 3:1 to 5:1, most preferably from 3.5:1 to 4.5:1.

28. The method according to any one of paragraphs 22 to 27, in step (a), an atomic ratio of transition metal to boron in the mixture is from 0.02:1 to 0.5:1.

29. The method according to any one of paragraphs 22 to 28, in step (a), a reaction temperature of the mixture is from 400° C. to 1100° C., preferably from 600° C. to 1000° C., most preferably from 800° C. to 900° C.; and a preferred reaction pressure is from 0.2 MPa to 10 MPa, preferably from 0.5 MPa to 5 MPa.

30. The method according to any one of paragraphs 22 to 29, in step (a), a reaction time of the mixture is from 1 h to 20 h, preferably from 10 h to 12 h.

31. The method according to any one of paragraphs 22 to 30, in step (b), the polar solvent is selected from water, methanol, ethanol, propanol, tetrahydrofuran, dimethylformamide or any mixture thereof.

32. The method according to paragraph 21, wherein the nitride carrier is a silicon nitride carrier, which is prepared by a thermochemical synthesis method comprising the following steps: (a') reacting a mixture of a silicon precursor and a nitrogen precursor in a sealed autoclave in the presence of an organic solvent, to give a crude product containing silicon nitride; (b') leaching the crude product containing silicon nitride obtained in step (a') with a mineral acid, to give an acid-leached crude product containing silicon nitride; (c') washing the acid-leached crude product containing silicon nitride with deionized water and solvent respectively and filtering, to give silicon nitride powder; (d') drying and calcining the silicon nitride powder to give the silicon nitride carrier.

33. The method according to paragraph 32, wherein the silicon precursor is selected from silicon tetrachloride, tetraethyl orthosilicate, methyl orthosilicate, silane, silane coupling agent, silaimines or any mixture thereof.

34. The method according to paragraph 32 or 33, in step (a'), the organic solvent is selected from benzene, toluene, xylene, ethylbenzene, hexane, heptane, octane, decane, liquid paraffin, trioctylamine or any mixture thereof.

35. The method according to any one of paragraphs 32 to 34, in step (a'), an atomic ratio of nitrogen to silicon in the mixture is (0.01-10):1, preferably (0.1-5):1, most preferably (0.2-1):1.

36. The method according to any one of paragraphs 32 to 35, in step (a'), a volume ratio of the organic solvent to the silicon precursor is (0.1-10):1, preferably (0.5-5):1, most preferably (1-2):1.

37. The method according to any one of paragraphs 32 to 36, in step (a'), a reaction temperature of the mixture is from 300° C. to 600° C., preferably from 400° C. to 500° C.; a preferred reaction pressure is 0.2-10 MPa, preferably 0.5-5 MPa.

38. The method according to any one of paragraphs 32 to 37, in step (a'), a reaction time of the mixture is from 1 h to 20 h, preferably from 5 h to 10 h.

39. The method according to any one of paragraphs 32 to 38, in step (c'), the solvent is selected from methanol, ethanol, propanol, tetrahydrofuran, dimethylformamide, or any mixture thereof.

40. The method according to any one of paragraphs 22 to 39, wherein the nitrogen precursor is selected from sodium azide, sodium amide, polycyanamide, guanidine, urea, ammonia, borazine, ammonium chloride or any mixture thereof.

41. The method according to any one of paragraphs 22 to 40, wherein the mineral acid is selected from hydrochloric acid, sulfuric acid, and nitric acid.

42. The method according to paragraph 41, wherein a concentration of the mineral acid is from 0.1 to 5 mol/L, preferably from 0.5 to 2.5 mol/L, most preferably from 1.0 to 1.5 mol/L.

43. The method according to any one of paragraphs 22 to 42, wherein the boron nitride powder or the silicon nitride powder is dried and calcined in air, in an inert atmosphere or in vacuum.

44. The method according to any one of paragraphs 22 to 43, in step (c) and step (d'), a temperature of the drying is from 20° C. to 150° C., preferably from 80° C. to 150° C.; and a preferred duration for the drying can be from 1 h to 24 h, preferably from 8 h to 12 h.

45. The method according to any one of paragraphs 22 to 44, in step (c) and step (d'), a temperature for the calcining is from 250° C. to 650° C., preferably from 350° C. to 600° C., most preferably from 450° C. to 550° C.; and a preferred duration for the calcining is from 1 h to 6 h.

46. The method according to paragraph 21, wherein the nitride carrier is obtained by ball milling or ultrasonication.

47. The method according to any one of paragraphs 18 to 46, wherein the precursor of the active metal and the precursor of the auxiliary metal are supported on the nitride carrier by impregnation, co-precipitation, water/solvent thermal synthesis, chemical vapor deposition, and/or atomic layer deposition.

48. The method according to any one of paragraphs 18 to 47, wherein the precursor of the active metal is one or more selected from ferric nitrate (preferably ferric nitrate nonahydrate), ferric chloride (preferably ferric chloride hexahydrate), ferrous chloride, ferrous sulfate, ferrous acetate. iron(III) acetylacetonate, carbonyl iron, ferrocene, cobalt nitrate (preferably cobalt nitrate hexahydrate), cobalt chloride (preferably cobalt chloride hexahydrate), cobalt formate, cobalt acetate, cobalt acetylacetonate, cobalt carbonyl, nickel nitrate, nickel chloride, nickel sulfate, nickel acetate, nickel acetylacetonate, nickel carbonyl, ruthenium chloride, ruthenium nitrate, triphenylphosphine chlorocarbonylruthenium, carbonyl ruthenium chloride, ammonium chlororuthenate, ruthenium nitrosyl nitrate.

49. The method according to any one of paragraphs 18 to 48, wherein the precursor of the auxiliary metal is one or more selected from manganese nitrate, manganese chloride, manganese acetate, manganese acetylacetonate, manganese carbonyl, zinc nitrate, zinc chloride, zinc sulfate, zinc acetate, zinc acetylacetonate, chromium nitrate, chromium chloride, chromium sulfate, ammonium molybdate (preferably ammonium heptamolybdate), platinum chloride, platinum nitrate, chloroplatinic acid, ammonium chloroplatinate, diammine platinum nitrite, rhodium nitrate, rhodium chloride, rhodium sulfate, rhodium acetate, tris(triphenylphosphine) rhodium chloride, acetylacetonatocarbonyltriphenylphosphinerhodium, palladium nitrate, palladium chloride, palladium sulfate, palladium acetate, ammonium tetrachloropalladate, ammonium hexachloropalladate, triphenylphosphine palladium, chloroiridic acid, iridium chloride, iridium acetate, ammonium chloroiridate, gold chloride, chloroauric acid, ammonium chloroaurate, silver nitrate, silver acetate, silver carbonate, magnesium nitrate, magnesium chloride, magnesium acetate, calcium nitrate, calcium chloride, calcium acetate, strontium nitrate, strontium chloride, strontium acetate, sodium nitrate, sodium chloride, sodium acetate, sodium hydroxide, sodium carbonate, sodium bicarbonate, potassium nitrate, potassium chloride, potassium hydroxide, potassium carbonate, potassium bicarbonate, potassium acetate.

50. The method according to any one of paragraphs 18 to 49, wherein the catalyst precursor formed in step (2) is dried and calcined prior to step (3).

51. The method according to any one of paragraphs 18 to 50, in step (3), the catalyst precursor is molded by a molding method selected from spray drying, compression molding, rotational molding, extrusion molding or molding in oil.

52. The method according to any one of paragraphs 18 to 51, wherein the molded catalyst precursor is in a form of particles, microspheres, sheets, strips, columns, rings, porous sheets, clover shapes.

53. The method according to any one of paragraphs 18 to 52, wherein the molded catalyst precursor is dried in air, in an inert atmosphere, or in vacuum.

54. The method according to any one of paragraphs 18 to 53, in step (4), a temperature for the drying is from 20° C. to 150° C., preferably from 80° C. to 150° C.; and a preferred duration for the drying is from 1 h to 24 h, preferably from 8 h to 12 h.

55. The method according to any one of paragraphs 18 to 54, in step (4), the molded catalyst precursor is dried twice or more.

56. The method according to any one of paragraphs 18 to 55, wherein the molded catalyst precursor is calcined in an inert atmosphere or an oxidizing atmosphere.

57. The method according to any one of paragraphs 18 to 56, in step (4), a temperature for the calcining is from 250° C. to 650° C., preferably from 350° C. to 600° C., most preferably from 450° C. to 550° C.; and a preferred duration for the calcining is from 1 h to 6 h.

58. The method according to any one of paragraphs 18 to 57, wherein the molded catalyst precursor is calcined twice or more.

59. Use of the Fischer-Tropsch synthesis catalyst according to any one of paragraphs 1-17 for preparing hydrocarbon compounds by catalyzing syngas in a Fischer-Tropsch synthesis reaction.

60. The use according to paragraph 59, wherein the catalyst is previously reduced in a reducing atmosphere prior to application of the catalyst to the Fischer-Tropsch synthesis reaction.

61. The use according to paragraph 60, wherein the reducing atmosphere is selected from a pure hydrogen atmosphere, a CO atmosphere, a syngas atmosphere, an ammonia gas atmosphere, a diluted hydrogen atmosphere, a diluted CO atmosphere, a diluted syngas atmosphere, and a diluted ammonia atmosphere.

62. The use according to paragraph 61, wherein the volume ratio of $H_2$ to CO in the syngas atmosphere is from 0.01:1 to 1000:1.

63. The use according to paragraph 59 or 60, wherein the volume ratio of $H_2$ to CO in the syngas is from 0.5:1 to 3.0:1, preferably from 1.0:1 to 2.5:1, more preferably from 1.2:1 to 2.2:1, most preferably from 1.5:1 to 2.0:1.

64. The use according to any one of paragraphs 59 to 63, wherein the Fischer-Tropsch synthesis reaction is carried out in a continuous reaction process or a batch reaction process.

65. The use according to any one of paragraphs 59 to 64, wherein the Fischer-Tropsch synthesis reaction is carried out in the continuous reaction process, and a reaction space velocity is 100-60000 NL/Kg/h.

66. The use according to any one of paragraphs 59 to 65, wherein the Fischer-Tropsch synthesis reaction is carried out by using one or more fixed bed reactors, microchannel reactors, continuous stirred slurry bed tank reactors, jet circulation reactors, slurry bubble column reactors or fluidized bed reactors.

67. The use according to any one of paragraphs 59 to 66, wherein a pressure of the Fischer-Tropsch synthesis reaction is from 1.0 MPa to 6.0 MPa and a temperature thereof is from 120° C. to 350° C.

68. The use according to paragraph 59 or 60, wherein the Fischer-Tropsch synthesis catalyst is a cobalt catalyst, and the volume ratio of $H_2$ to CO in the syngas is from 1.0:1 to 3.0:1, preferably from 1.5:1 to 2.5:1, most preferably from 1.8:1 to 2.2:1.

69. The use according to paragraph 68, wherein a pressure of the Fischer-Tropsch synthesis reaction is from 1.0 MPa to 6.0 MPa, preferably from 1.5 MPa to 4.5 MPa, most preferably from 2.0 MPa to 3.0 MPa; and a preferred temperature thereof is from 150° C. to 280° C., preferably from 180° C. to 260° C., most preferably from 200° C. to 240° C.

70. The use according to paragraph 68 or 69, wherein the Fischer-Tropsch synthesis reaction is carried out in the continuous reaction process, and a reaction space velocity is from 100 to 25,000 NL/kg/h, preferably from 1,000 to 20,000 NL/kg/h, most preferably from 5,000 to 10,000 NL/Kg/h.

71. The use according to paragraph 59 or 60, wherein the Fischer-Tropsch synthesis catalyst is an iron catalyst, and the volume ratio of $H_2$ to CO in the syngas is from 0.5:1 to 3.0:1, preferably from 1.0:1 to 2.5:1, more preferably from 1.2:1 to 2.2:1, most preferably from 1.5:1 to 2.0:1.

72. The use according to paragraph 71, wherein a pressure of the Fischer-Tropsch synthesis reaction is from 1.0 MPa to 6.0 MPa, preferably from 1.5 MPa to 5.5 MPa, more preferably from 2.0 MPa to 5.0 MPa, most preferably from 2.5 MPa to 4.0 MPa; and a temperature thereof is from 220° C. to 350° C., preferably from 240° C. to 330° C., most preferably from 260° C. to 300° C.

73. The use according to paragraph 71 or 72, wherein the Fischer-Tropsch synthesis reaction is carried out in the continuous reaction process, and a reaction space velocity is from 100 to 60,000 NL/kg/h, preferably from 1,000 to 40,000 NL/kg/h, most preferably from 10,000 to 20,000 NL/Kg/h.

The present invention is not limited to the preferred embodiments and examples described herein, and those skilled in the art can modify these embodiments and applications as long as they do not depart from the purpose of the invention.

EXAMPLE

Example 1

Hexagonal boron nitride carrier with a high specific surface area was prepared by ball milling: 20 g of commercialized hexagonal boron nitride (purity of 99.0%, particle size of 5 μm, specific surface area of 21 m²/g, Qingzhou Fangyuan Boron Nitride Factory), 200 ml of ethanol, 65 ml of zirconia beads (0.5 mm) were added to a 500 ml zirconia grinding tank and it was sealed, the air in the tank was replaced with nitrogen and they were ground at 300 rpm for 24 h. The obtained boron nitride powder was not washed with deionized water and filtered, but dried overnight at 80° C., and then calcined in a muffle furnace at 500° C. for 5 h, and the obtained hexagonal boron nitride (h-BN) was labeled as Exam-1, the XRD pattern thereof was shown in FIG. 1, and the texture properties were listed in Table 1.

Example 2

Figure 2:
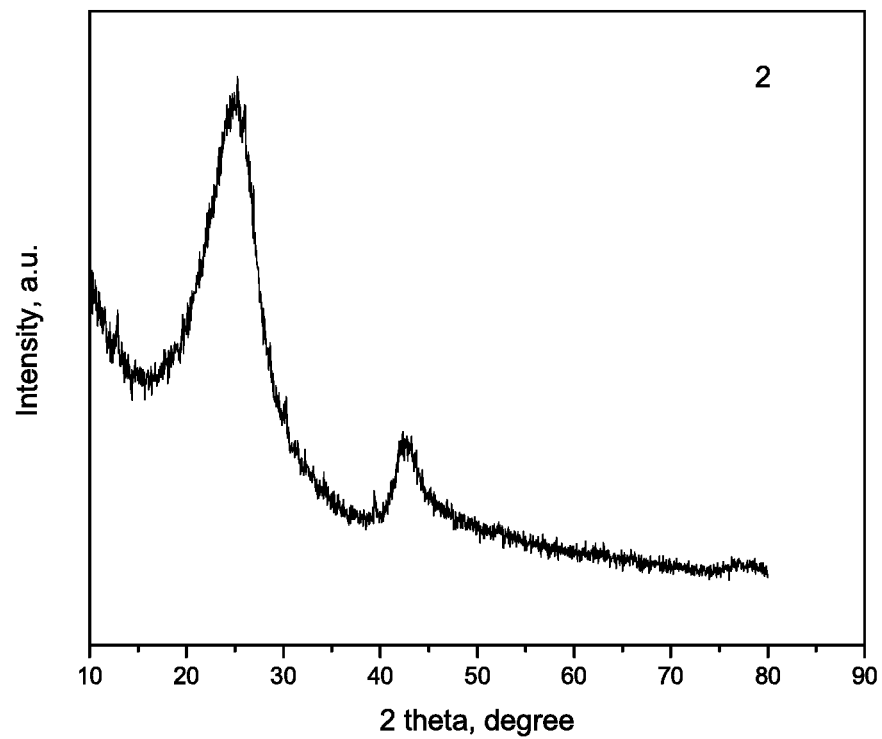
FIG. 2 is XRD pattern of the boron nitride carrier prepared in Example 2.

The boron nitride carrier was prepared by the following method: 17.4 g of $B_2O_3$, 75.1 g of urea and 2.8 g of $Fe_2O_3$ were uniformly ground, placed in a 500 ml stainless steel autoclave and sealed. The autoclave was heated to 1000° C. at a heating rate of 10° C./min and kept for 5 hours to carry out the reaction, and the reaction pressure was 9.5 MPa. The obtained sample powder was washed with 3M hydrochloric acid solution and filtered, and repeatedly washed with ethanol and deionized water to remove impurity elements, then dried in an oven at 80° C. overnight, and finally heated to 500° C. at a heating rate of 5° C./min in a muffle furnace and calcined at this temperature for 5 h. The resulting BN carrier was labeled as Exam-2, the XRD pattern thereof was shown in FIG. 2, and the texture properties were listed in Table 1.

Example 3

Figure 3:
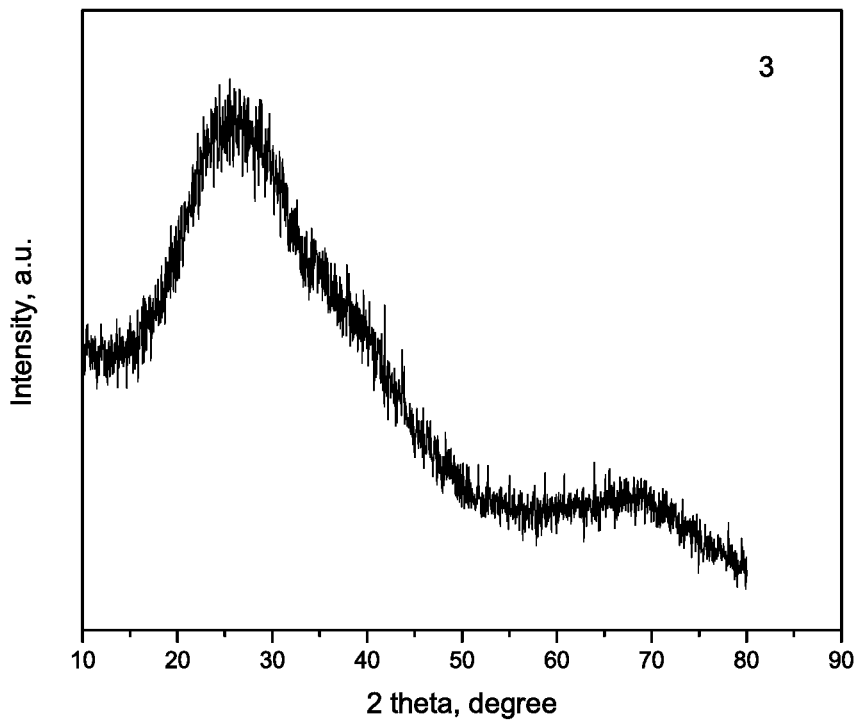
FIG. 3 is XRD pattern of the silicon nitride carrier prepared in Example 3.

Silicon nitride carrier ($Si_3N_4$) was prepared by an ultrasonic method: 20 g of commercialized silicon nitride (purity of 99.0%, specific surface area of 71 m²/g, Qinhuangdao Yinuo Advanced Material Development Co., Ltd.) and 400 ml of deionized water were mixed and stirred into a slurry, placed in a 1000 ml ultrasonic cup, and crushed under ultrasound (power of 150 W) for 8 h, then washed with deionized water, filtered, dried overnight in an oven at 110° C., and finally heated to 500° C. at a heating rate of 5° C./min in a muffle furnace and calcined at this temperature for 5 h. The resulting silicon nitride carrier was labeled as Exam-3, XRD pattern thereof was shown in FIG. 3, and the texture properties were listed in Table 1.

Example 4

A cobalt-based catalyst supported on boron nitride and silicon nitride was prepared by an impregnation method: 4.93 g of cobalt nitrate hexahydrate (Co loading of 10 wt %) was weighed and dissolved in deionized water, and respectively impregnated onto 10 g of h-BN, BN and $Si_3N_4$ carriers prepared in Example 1, Example 2 and Example 3 at a volume ratio of 1:1, standing still for 8 hours, dried in an oven at 110° C. overnight, heated to 350° C. at a heating rate of 1° C./min in a muffle furnace and calcined at this temperature for 2 hours, and the composition of each catalyst in the oxidation state is 10Co/100BN, 10Co/100BN and 10Co/100$Si_3N_4$, which were respectively labeled as Exam-4a, Exam-4b and Exam-4c, and texture properties, degrees of reduction and dispersity thereof were listed in Table 1.

Fischer-Tropsch synthesis performance test: 0.5 g of each of the abovementioned catalyst was taken, diluted and uniformly mixed with 2 ml of silicon carbide, and placed in a fixed bed reactor having an inner diameter of 10 mm and a constant temperature section of 50 mm in length. The catalyst was reduced in $H_2$ at 375° C. for 6 hours and cooled down to 160° C. Then, the syngas of 64% $H_2$/31% CO/5% Ar (volume ratio) was introduced into the reactor at a pressure of 2.0 MPa, and the reactor temperature was increased to 220° C. at a heating rate of 0.1° C./m in, the reaction space velocity was adjusted to 5,000 NL/Kg/h, and the reaction was maintained for 100 hours or more. Then, the reaction temperature was raised to 250° C., the space velocity was adjusted to 12,000 NL/Kg/h, and the reaction was carried out for about 50 hours while maintaining the conditions; then the temperature was lowered to 220° C., the space velocity was adjusted to 5000 NL/Kg/h, and the reaction was maintained for 24 hours or more. The composition of the reactor off-gas was analyzed by using a gas chromatography during the reaction, and used to calculate the CO conversion rate, product selectivity and stability. The result of the Fischer-Tropsch synthesis reaction of each of the abovementioned catalyst was listed in Table 2.

Example 5

20Co1Mn0.1Ru/100BN catalyst was prepared by an impregnation method: 9.88 g of cobalt nitrate hexahydrate (Co loading of 20 wt %), 0.52 g of manganese nitrate (50 wt %), 0.67 g of ruthenium nitrosyl nitrite solution (concentration of 1.5 wt %) were weighed and dissolved in deionized water, impregnated onto 10 g of the BN carrier prepared in Example 2 according to a volume ratio of 1:1, standing still for 8 hours, dried overnight at 110° C. in a nitrogen atmosphere, and heated to 350° C. at a heating rate of 1° C./min in a muffle furnace and calcined for 2 hours. The composition of the obtained catalyst in the oxidation state was 20Co1Mn0.1Ru/100BN, which was labeled as Exam-5, and texture properties, degrees of reduction and dispersity thereof were listed in Table 1. The Fischer-Tropsch synthesis performance test was carried out in the same manner as that in Example 4, and the results were listed in Table 2.

Example 6

A cobalt-based catalyst supported on boron nitride was prepared by a co-precipitation method: 24.71 g of cobalt nitrate hexahydrate, 5.18 g of 50% manganese nitrate solution, 0.01 g of platinum chloride were weighed and dissolved in 100 mL of deionized water, and then 10 g of boron nitride carrier prepared in Example 2 was weighed and mixed with the above solution to form a uniform suspension by ultrasonic dispersion. 1 mol/L aqueous solution of ammonia was added dropwise to the above suspension under stirring until a pH of 8-9 to form a precipitate. The precipitate was filtered, washed, dried overnight at 120° C. in air, heated to 450° C. at a heating rate of 1° C./min in a muffle furnace and calcined at this temperature for 5 hours, to obtain a catalyst in oxidation state with a composition of 50Co10Mn0.06Pt/100BN, which was labeled as Exam-6, and texture properties, degrees of reduction and dispersity thereof were listed in Table 1.

The Fischer-Tropsch synthesis performance test was carried out in the same manner as that in Example 4, and the results were listed in Table 2.

Example 7

A cobalt-based catalyst supported on boron nitride was prepared by an impregnation method: except that the amount of cobalt nitrate hexahydrate was 12.35 g, manganese nitrate was replaced with 0.72 g of ferric nitrate nonahydrate, and ruthenium nitrosyl nitrate was replaced with 0.02 g of palladium nitrate, amounts of other materials and other operating conditions were the same as those in Example 5. The composition of the obtained catalyst in the oxidation state was 25Co1Fe0.1Pd/100BN, which was labeled as Exam-7, and texture properties, degrees of reduction and dispersity thereof were listed in Table 1.

The Fischer-Tropsch synthesis performance test was carried out in the same manner as that in Example 4, and the results were listed in Table 2.

Example 8

10Co2Mn0.07Ir/100BN catalyst was prepared by an impregnation method: except that cobalt nitrate was replaced with 4.04 g of cobalt chloride, manganese nitrate was replaced with 0.47 g of manganese chloride and ruthenium nitrosyl nitrate was replaced with 0.01 g of iridium chloride, amounts of other materials and other operating conditions were the same as those in Example 5. The composition of the obtained catalyst in the oxidation state was 10Co2Mn0.07Ir/100BN, which was labeled as Exam-8, and texture properties, degrees of reduction and dispersity thereof were listed in Table 1.

The Fischer-Tropsch synthesis performance test was carried out in the same manner as that in Example 4, and the results were listed in Table 2.

Example 9

A cobalt catalyst supported on boron nitride was prepared by a co-precipitation method, except that the following parameters and conditions were adjusted, amounts of other materials and other operating conditions were the same as those in Example 6; the composition of the obtained catalyst in the oxidation state was 100Co8Zn0.05Au/100BN, which was labeled as Exam-9, and texture properties, degrees of reduction and dispersity thereof were listed in Table 1: cobalt nitrate was replaced with 40.37 g of cobalt chloride hexahydrate, manganese nitrate was replaced with 1.66 g of zinc chloride, and platinum chloride was replaced with 0.015 g of 50% gold chloride solution, which were dissolved in 500 mL of deionized water.

The Fischer-Tropsch synthesis performance test was carried out in the same manner as that in Example 4, and the results were listed in Table 2.

Example 10

A cobalt catalyst supported on boron nitride was prepared by a co-precipitation method, and except that the following parameters and conditions were adjusted, amounts of other materials and other operating conditions were the same as those in Example 6; the composition of the obtained catalyst in the oxidation state was 200Co25Zn0.04Rh/100BN, which was labeled as Exam-10, and texture properties, degrees of reduction and dispersity thereof were listed in Table 1: cobalt nitrate was replaced with 80.75 g of cobalt chloride hexahydrate, manganese nitrate was replaced with 5.20 g of zinc chloride, and platinum chloride was replaced with 0.01 g of rhodium chloride, which were dissolved in 500 mL of deionized water.

The Fischer-Tropsch synthesis performance test was carried out in the same manner as that in Example 4, and the results were listed in Table 2.

Example 11

Figure 4:
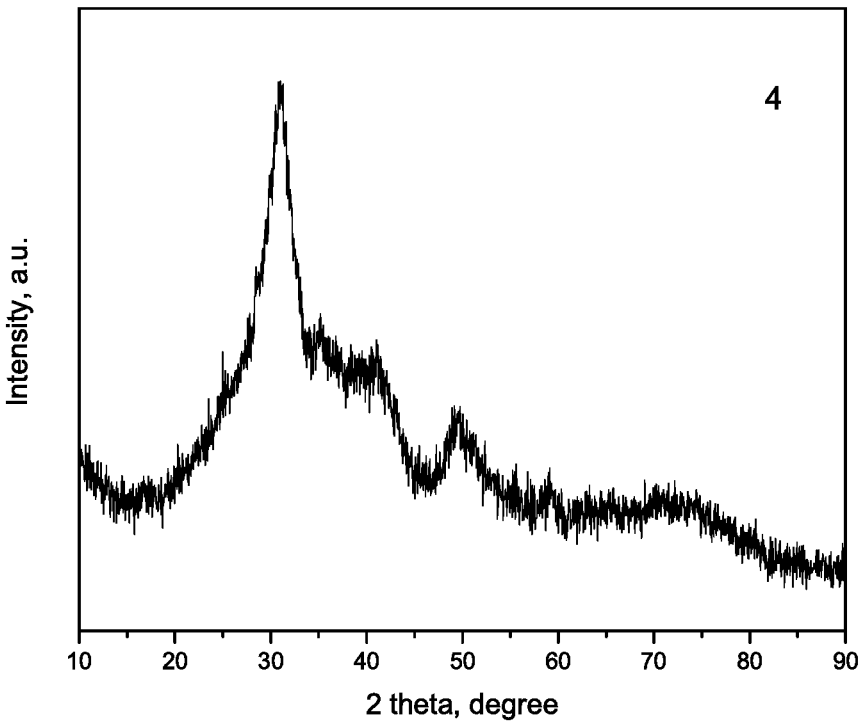
FIG. 4 is XRD pattern of catalyst Exam-11a prepared in Example 11.
Figure 5:
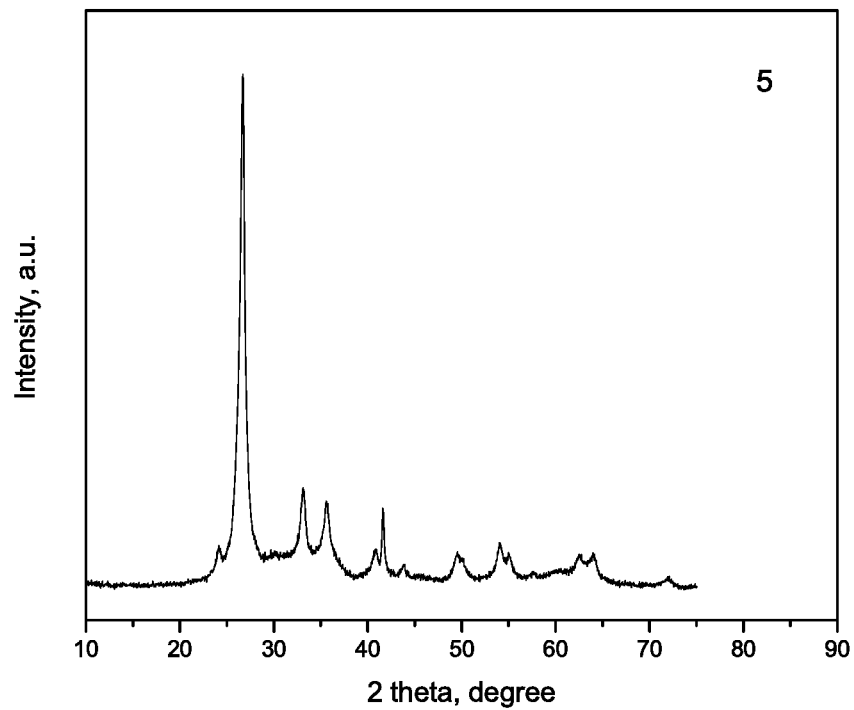
FIG. 5 is XRD pattern of catalyst Exam-11b prepared in Example 11.
Figure 6:
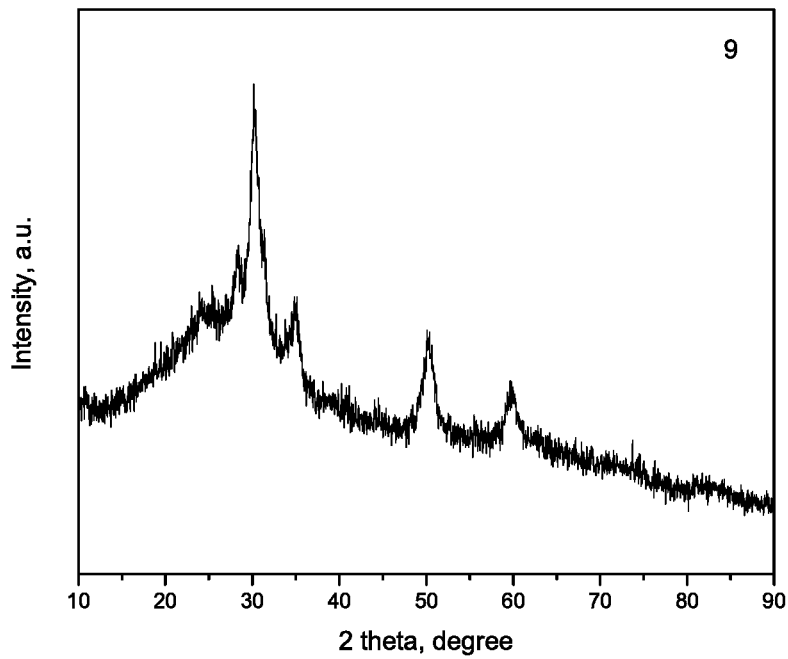
FIG. 6 is XRD pattern of catalyst Exam-11c prepared in Example 11.

Except that cobalt nitrate was replaced with 7.23 g of ferric nitrate, amounts of other materials and other operating conditions were the same as those in Example 4, to give the catalysts in the oxidation state with the compositions of 10Fe/100BN, 10Fe/100BN and 10Fe/100BN, which were respectively labeled as Exam-11a, Exam-11b and Exam-11c, the texture properties, degrees of reduction and dispersity thereof were listed in Table 1. The XRD patterns of the three catalysts were shown in FIGS. 4, 5 and 6. The active metal was present in a highly dispersed iron oxide structure with a grain size between 2 nm and 9 nm.

Fischer-Tropsch synthesis performance test: 0.5 g of each of the abovementioned catalyst was weighed, diluted and uniformly mixed with 2 mL of silicon carbide, and placed in a fixed bed reactor having an inner diameter of 10 mm and a constant temperature section of 50 mm in length. The catalyst was reduced in the syngas of 98% $H_2$/2% CO at 320° C. for 24 hours and cooled down to 220° C. Then, the syngas of 63% $H_2$/37% CO was introduced into the reactor at a pressure of 2.0 MPa, and the reactor temperature was increased to 280° C. at a heating rate of 0.1° C./m in, the reaction space velocity was adjusted to 15,000 NL/Kg/h, and the reaction was maintained for 100 hours or more. Then, the reaction temperature was raised to 300° C., the space velocity was adjusted to 36,000 NL/Kg/h, the reaction was carried out for about 50 hours while maintaining the conditions; then the temperature was lowered to 280° C., the space velocity was adjusted to 15,000 NL/Kg/h, and the reaction was maintained for 24 hours or more. The composition of the reactor off-gas was analyzed by using a gas chromatography during the reaction, and used to calculate the CO conversion rate, product selectivity and stability. The results of the Fischer-Tropsch synthesis reaction were listed in Table 2.

Example 12

Except that cobalt nitrate was replaced with 14.47 g of ferric nitrate nonahydrate, amount of manganese nitrate was increased to 1.31 g, ruthenium nitrosyl nitrate was replaced with 0.29 g of copper nitrate and 0.37 g of sodium nitrate was added, amounts of other materials and other operating conditions were the same as those in Example 5, to give the catalyst in the oxidation state with the composition of 20Fe2.5Mn0.2Cu1Na/100BN, which was labeled as Exam-12, the texture properties, degrees of reduction and dispersity thereof were listed in Table 1.

The Fischer-Tropsch synthesis performance test was carried out in the same manner as that in Example 11, and the results were listed in Table 2.

Example 13

Except for the following adjustments, amounts of other materials and other operating conditions were the same as those in Example 12, to give the catalyst in the oxidation state with the composition of 30Fe1Mo0.06Pt0.5K/100BN, which was labeled as Exam-13, the texture properties, degrees of reduction and dispersity thereof were listed in Table 1: ferric nitrate nonahydrate was replaced with 14.52 g of ferric chloride hexahydrate, manganese nitrate was replaced with 0.18 g of ammonium heptamolybdate, copper nitrate was replaced with 0.01 g of platinum chloride, sodium nitrate was replaced with 0.10 g of potassium chloride; ammonium heptamolybdate was firstly supported on the boron nitride carrier prepared in Example 2, and other metal salts described above were supported on the carrier by a step-by-step impregnation method.

The Fischer-Tropsch synthesis performance test was carried out in the same manner as that in Example 11, and the results were listed in Table 2.

Example 14

An iron-based catalyst supported on boron nitride was prepared by a co-precipitation method, except that the following parameters and conditions were adjusted, amounts of other materials and other operating conditions were the same as those in Example 9, and the composition of the obtained catalyst in the oxidation state was 100Fe5Cr0.1Pd5Mg/100BN, which was labeled as Exam-14, texture properties, degrees of reduction and dispersity thereof were listed in Table 1: cobalt chloride hexahydrate was replaced with 72.35 g of iron nitrate nonahydrate, zinc chloride was replaced with 3.85 g of chromium nitrate, gold chloride was replaced with 0.02 g of palladium nitrate, and 3.05 g of magnesium nitrate was added, which were dissolved in 500 ml of deionized water.

The Fischer-Tropsch synthesis performance test was carried out in the same manner as that in Example 11, and the results were listed in Table 2.

Example 15

An iron-based catalyst supported on boron nitride was prepared by a co-precipitation method, except that the following parameters and conditions were adjusted, amounts of other materials and other operating conditions were the same as those in Example 9, and the composition of the obtained catalyst in the oxidation state was 200Fe8Zr0.07Ir5Ca/100BN, which was labeled as Exam-15, texture properties, degrees of reduction and dispersity were listed in Table 1: cobalt chloride hexahydrate was replaced with 96.81 g of ferric chloride hexahydrate, zinc chloride was replaced with 2.84 g of zirconyl chloride, gold chloride was replaced with 0.01 g of iridium chloride, and 2.75 g of calcium chloride was added, which were dissolved in 500 ml of deionized water.

The Fischer-Tropsch synthesis performance test was carried out in the same manner as that in Example 11, and the results were listed in Table 2.

Example 16

An iron-based catalyst supported on boron nitride was prepared by a co-precipitation method, except that the following parameters and conditions were adjusted, amounts of other materials and other operating conditions were the same as those in Example 9, and the composition of the obtained catalyst in the oxidation state was 300Fe40Mn15Cu5Sr/100BN, and the catalyst was labeled as Exam-16; texture properties, degrees of reduction and dispersity thereof were listed in Table 1: cobalt chloride hexahydrate was replaced with 217.0 g of iron nitrate nonahydrate, zinc chloride was replaced with 20.9 g of manganese nitrate, gold chloride was replaced with 13.43 g of copper nitrate, 2.40 g of strontium chloride was added, which were dissolved in 500 ml of deionized water; then 10 g of the boron nitride carrier prepared in Example 2 was weighed and mixed with the above solution, to form a uniform suspension by using ultrasonic dispersion; 1 mol/L aqueous solution of ammonia was added dropwise into the suspension under stirring to a pH of 8-9 to form a precipitate; the precipitate was filtered, washed, and dried at 120° C. overnight, heated to 450° C. at a heating rate of 1° C./m in in a muffle furnace and calcined at this temperature for 5 hours. The Fischer-Tropsch synthesis performance test was carried out in the same manner as that in Example 11, and the results were listed in Table 2.

Comparative Example 1

Except that the h-BN, BN and silicon nitride carriers prepared in Example 1, Example 2 and Example 3 were replaced with commercialized silicon nitride (Qinhuangdao Yinuo Advanced Material Development Co., Ltd., purity >99.0%, specific surface area of 70 m$^2$/g), amounts of other materials and other operating conditions were the same as those in Example 4. The composition of the obtained catalyst in the oxidation state was 10Co/100Si$_3$N$_4$, which was labeled as CE-4, and texture properties, degrees of reduction and dispersity thereof were listed in Table 1. The Fischer-Tropsch synthesis performance test was carried out in the same manner as that in Example 4, and the results were listed in Table 2.

Comparative Example 2

Except that the h-BN, BN and silicon nitride carriers prepared in Example 1, Example 2 and Example 3 were replaced with commercialized boron nitride (Qingzhou Fangyuan Boron Nitride Factory, purity 99.0%, specific surface area of 21 m$^2$/g), amounts of other materials and other operating conditions were the same as those in Example 11. The composition of the obtained catalyst in the oxidation state was 10Fe/100BN, which was labeled as CE-3, and texture properties, degrees of reduction and dispersity thereof were listed in Table 1. The Fischer-Tropsch synthesis performance test was carried out in the same manner as that in Example 4, and the results were listed in Table 2.

Comparative Example 3

Except that the silicon nitride carrier prepared in Example 2 was replaced with 13.3 g of pseudo-boehmite (produced by Shandong Aluminum Co., Ltd., containing 75 wt % of dry-basis alumina), amounts of other materials and other operating conditions were the same as those in Example 6. The composition of the obtained catalyst in the oxidation state was 25Co5Mn0.06Pt/100Al$_2$O$_3$, which was labeled as CE-1, and texture properties, degrees of reduction and dispersity thereof were listed in Table 1. The Fischer-Tropsch synthesis performance test was carried out in the same manner as that in Example 4, and the results were listed in Table 2.

Comparative Example 4

Except that the silicon nitride carrier prepared in Example 2 was replaced with 10.0 g of white carbon black (Shanghai Yuejiang Titanium Dioxide Chemical Co., Ltd., purity 99.8%, specific surface area 300 m$^2$/g), amounts of other materials and other operating conditions were the same as those in Example 13. The composition of the obtained catalyst in the oxidation state was 30Fe1Mo0.06Pt0.5K/100SiO$_2$, which was labeled as CE-2, and texture properties, degrees of reduction and dispersity thereof were listed in Table 1. The Fischer-Tropsch synthesis performance test was carried out in the same manner as that in Example 11, and the results were listed in Table 2.

Comparative Example 5

A hexagonal boron nitride supported iron catalyst used for the Fischer-Tropsch synthesis reaction was prepared according to the method disclosed in the document *RSC Advances*, 2016, 6, pp. 38356-38364, and the composition of the obtained catalyst was 33Fe/100BN, which was labeled as CE-5. The texture properties, degrees of reduction and dispersity thereof were listed in Table 1. The Fischer-Tropsch synthesis performance test was carried out in the same manner as that in Example 11, and the results were listed in Table 2.

TABLE 1

Texture properties, degrees of reduction and dispersity of each carrier and catalyst prepared in Examples 1-16 and Comparative Examples 1-5

| Sample | specific surface area m$^2$/g | Average pore size nm | Metal particle size nm | Degree of Reduction % | metal dispersity % |
|---|---|---|---|---|---|
| Exam-1 | 131 | 13.88 | — | — | — |
| Exam-2 | 629 | 8.57 | — | — | — |
| Exam-3 | 242 | 8.31 | — | — | — |
| Exam-4a | 85 | 11.49 | 7.8 | 76.7 | 17.3 |
| Exam-4b | 407 | 6.28 | 2.3 | 82.6 | 58.6 |
| Exam-4c | 178 | 7.93 | 8.7 | 79.4 | 15.5 |
| Exam-5 | 383 | 7.14 | 4.9 | 85.7 | 27.5 |
| Exam-6 | 444 | 6.53 | 2.1 | 80.4 | 64.2 |
| Exam-7 | 337 | 6.98 | 4.6 | 86.6 | 29.3 |
| Exam-8 | 422 | 6.01 | 2.5 | 81.9 | 53.9 |
| Exam-9 | 275 | 7.33 | 5.3 | 87.2 | 25.4 |
| Exam-10 | 196 | 8.05 | 6.2 | 86.1 | 21.7 |
| Exam-11a | 87 | 11.6 | 6.7 | 76.1 | 23.7 |
| Exam-11b | 415 | 6.2 | 2.2 | 82.8 | 72.2 |
| Exam-11c | 176 | 7.9 | 8.8 | 78.9 | 18.1 |
| Exam-12 | 358 | 7.2 | 4.6 | 85.3 | 34.5 |
| Exam-13 | 397 | 6.5 | 4.2 | 80.7 | 37.8 |
| Exam-14 | 329 | 6.8 | 4.5 | 85.0 | 35.3 |
| Exam-15 | 272 | 7.3 | 6.2 | 88.5 | 25.6 |
| Exam-16 | 191 | 8.1 | 6.6 | 87.1 | 24.1 |
| CE-1 | 58 | 13.5 | 11.7 | 91.3 | 11.5 |
| CE-2 | 8 | 0.03 | 48 | 77.6 | 3.3 |

TABLE 1-continued

Texture properties, degrees of reduction and dispersity of each carrier and catalyst prepared in Examples 1-16 and Comparative Examples 1-5

| Sample | specific surface area m$^2$/g | Average pore size nm | Metal particle size nm | Degree of Reduction % | metal dispersity % |
|---|---|---|---|---|---|
| CE-3 | 241 | 7.2 | 6.4 | 93.1 | 21.1 |
| CE-4 | 159 | 8.2 | 15 | 92.6 | 10.6 |
| CE-5 | 50 | — | 25 | — | 5.0 |

— indicated that the relevant item was not tested

TABLE 2

Fischer-Tropsch synthesis reactivity, selectivity and stability of the catalysts prepared in Examples 1-16 and Comparative Examples 1-5

| Catalyst | temperature °C. | space velocity, NL/Kg/h | test period, h | CO conversion rate, % | CO$_2$ selectivity, % | hydrocarbon selectivity, wt % | | stability |
|---|---|---|---|---|---|---|---|---|
| | | | | | | CH$_4$ | C$_5^+$ | |
| Exam-4a | 220 | 8000 | 15-121 | 19.6 | 0 | 8.4 | 75.7 | 0.78 |
| | 250 | 15000 | 126-165 | 52.1 | 0.2 | 11.8 | 71.2 | |
| | 220 | 8000 | 174-205 | 15.4 | 0 | 9.1 | 74.6 | |
| Exam-4b | 220 | 10000 | 8-119 | 25.3 | 0 | 6.5 | 80.2 | 0.94 |
| | 250 | 25000 | 124-166 | 58.3 | 0.1 | 10.7 | 73.8 | |
| | 220 | 10000 | 175-203 | 23.9 | 0 | 6.3 | 82.4 | |
| Exam-4c | 220 | 8000 | 12-120 | 15.7 | 0 | 9.3 | 77.5 | 0.74 |
| Exam-5 | 220 | 10000 | 13-122 | 32.8 | 0 | 3.6 | 90.3 | 0.92 |
| | 250 | 30000 | 127-169 | 59.1 | 0.1 | 8.3 | 73.7 | |
| | 220 | 10000 | 179-204 | 30.2 | 0 | 3.5 | 86.3 | |
| Exam-6 | 220 | 15000 | 11-118 | 25.8 | 0 | 4.2 | 80.5 | 0.99 |
| | 250 | 30000 | 123-170 | 48.6 | 0.1 | 7.9 | 68.8 | |
| | 220 | 15000 | 181-210 | 25.5 | 0 | 4.7 | 78.6 | |
| Exam-7 | 220 | 10000 | 9-119 | 23.9 | 0 | 3.4 | 89.7 | 0.86 |
| Exam-8 | 220 | 10000 | 6-122 | 28.4 | 0 | 3.5 | 95.6 | 1.01 |
| | 250 | 25000 | 127-171 | 55.8 | 0.1 | 6.6 | 89.2 | |
| | 220 | 10000 | 180-212 | 28.6 | 0 | 2.8 | 94.1 | |
| Exam-9 | 220 | 20000 | 10-123 | 22.7 | 0 | 2.9 | 95.8 | 0.53 |
| | 250 | 35000 | 128-169 | 49.3 | 0.1 | 5.2 | 90.6 | |
| | 220 | 20000 | 177-202 | 12.0 | 0 | 3.5 | 92.9 | |
| Exam-10 | 220 | 30000 | 5-128 | 32.7 | 0 | 2.8 | 94.7 | 0.69 |
| Exam-11a | 280 | 15000 | 2-48 | 18.5 | 5.2 | 18.4 | 55.7 | 0.83 |
| | 300 | 36000 | 52-101 | 54.7 | 8.7 | 23.8 | 41.2 | |
| | 280 | 15000 | 110-135 | 15.3 | 5.3 | 19.1 | 54.2 | |
| Exam-11b | 280 | 15000 | 6-46 | 26.8 | 4.5 | 16.5 | 60.2 | 0.90 |
| | 300 | 47500 | 50-99 | 57.3 | 8.1 | 21.7 | 53.9 | |
| | 280 | 15000 | 99-126 | 24.2 | 4.0 | 16.3 | 61.7 | |
| Exam-11c | 280 | 15000 | 5-119 | 15.4 | 5.5 | 19.3 | 49.1 | 0.79 |
| Exam-12 | 280 | 18000 | 3-47 | 26.4 | 6.8 | 4.6 | 85.3 | 0.95 |
| | 300 | 55500 | 51-100 | 57.5 | 8.5 | 8.1 | 78.5 | |
| | 280 | 18000 | 111-133 | 25.2 | 6.3 | 4.4 | 84.7 | |
| Exam-13 | 280 | 18000 | 4-47 | 22.3 | 7.2 | 3.2 | 89.5 | 0.99 |
| | 300 | 50000 | 51-98 | 49.5 | 9.1 | 5.5 | 88.8 | |
| | 280 | 18000 | 106-129 | 22.1 | 7.3 | 3.7 | 90.1 | |
| Exam-14 | 280 | 30000 | 2-109 | 29.9 | 8.6 | 5.4 | 83.7 | 0.86 |
| Exam-15 | 280 | 50000 | 5-110 | 32.7 | 8.1 | 4.5 | 85.6 | 0.78 |
| Exam-16 | 280 | 60000 | 10-123 | 28.1 | 7.2 | 4.9 | 85.8 | 0.74 |
| CE-1 | 220 | 8000 | 5-110 | 6.6 | 0 | 7.8 | 79.2 | 0.51 |
| CE-2 | 280 | 10000 | 2-108 | 7.3 | 22.4 | 21.7 | 39.3 | 0.37 |
| CE-3 | 220 | 5000 | 8-105 | 19.8 | 0.5 | 6.4 | 73.3 | 0.67 |
| CE-4 | 280 | 18000 | 3-107 | 13.6 | 28.2 | 3.7 | 89.1 | 0.71 |
| CE-5 | 280 | 1500 | 5-145 | 42-48 | 35.7 | 14.2 | 46.3 | 0.88 |

As shown in Table 2, the cobalt catalyst containing a boron nitride and/or silicon nitride carrier with a high specific surface area of the present invention exhibited very high Fischer-Tropsch synthesis catalytic activity and excellent C$_5^+$ hydrocarbon selectivity. After undergoing a long period of time (more than 200 h) and a high-temperature (250° C. or higher) harsh severe reaction, the activity of most catalysts can still be recovered to 80% or more of the initial activity, indicating that the catalyst of the present invention has good stability. In particular, the catalysts of Example 6 and Example 8 (Exam-6 catalyst and Exam-8 catalyst) exhibited the optimal Fischer-Tropsch synthesis catalytic performance. In contrast, activities and stabilities of CE-1 and CE-3 catalysts containing commercially available silicon nitride or $Al_2O_3$ carriers with low specific surface area were much less than those of Exam-4c and Exam-6 catalysts with similar metal active phase compositions.

Similarly, the iron catalyst containing the boron nitride and/or silicon nitride carrier with a high specific surface area prepared in the present invention exhibited higher Fischer-Tropsch synthesis catalytic activity and the same excellent $C_5^+$ hydrocarbon selectivity at higher reaction temperatures. After experiencing long-term and high-temperature reactions, the activity of these nitride-supported iron catalysts can be recovered to 70% or more of the initial activity, indicating that the catalyst of the present invention has excellent stability and catalytic activity. In particular, the Exam-13 catalyst has the same final Fischer-Tropsch synthesis reaction performance as the initial reaction performance thereof. In contrast, CE-2 and CE-4 catalysts containing commercially available boron nitride or $SiO_2$ carriers with a low specific surface area had poor activity and stability. In addition, compared with the results of the CE-5 catalyst of Comparative Example 5, it can be seen that the metal grain size (2-9 nm) of the catalyst prepared by the present invention is much smaller than the average size of the metallic iron (25-40 nm) of the catalyst prepared in the literature (*RSC Advances*, 2016, 6, pp. 38356-38364), and the dispersity of the active metal in the catalyst of the invention (15-70%) is also much greater than that (3-5%) of the catalyst reported in the literature. Thus, at the space velocity level much higher than that reported in the literature (10-40 times), the CO conversion rate of the catalyst of the present invention in the Fischer-Tropsch synthesis reaction can still be comparable to that reported in the literature, that is, the catalytic activity of the catalyst of the present invention is 10-40 times higher than that of the catalyst in the above literature, and selectivities of byproducts (methane and $CO_2$) are lower by using the catalyst of the present invention in the Fischer-Tropsch synthesis reaction.

It can thus be seen that the catalyst of the present invention containing a boron nitride carrier and/or a silicon nitride carrier with a high specific surface area can achieve very excellent Fischer-Tropsch synthesis reaction performance.

The invention claimed is:

1. A Fischer-Tropsch synthesis catalyst, wherein the catalyst comprises: an active component, which is at least one selected from iron and cobalt; an optional auxiliary metal; and a nitride carrier, which is boron nitride, silicon nitride or a mixture thereof having a specific surface area of not less than 80 m$^2$/g; wherein the active component and the optional auxiliary metal are supported on the carrier; and wherein a dispersity of the active component is from 15% to 75%, and the catalyst has a metal grain size of 2-9 nm.

2. The catalyst according to claim 1, wherein the boron nitride is a hexagonal boron nitride.

3. The catalyst according to claim 1, wherein the silicon nitride is a trigonal silicon nitride and/or a hexagonal silicon nitride.

4. The catalyst according to claim 1, wherein a mass ratio of the active component:the auxiliary metal:the carrier is (0.1-300):(0.002-30):100.

5. The catalyst according to claim 1, wherein the auxiliary metal is at least one selected from the group consisting of manganese, chromium, zinc, molybdenum, copper, platinum, palladium, rhodium, iridium, gold, silver, magnesium, calcium, strontium, barium, sodium and potassium.

6. The catalyst according to claim 1, wherein a mass ratio of the active component to the carrier is (0.1-400):100.

7. The catalyst according to claim 6, wherein the mass ratio of the active component to the carrier is (1-400):100.

8. The catalyst according to claim 1, wherein a mass ratio of the auxiliary metal to the carrier is (0.002-60):100.

9. The catalyst according to claim 8, wherein the auxiliary metal is at least one selected from the group consisting of manganese, chromium, molybdenum and zinc, and the mass ratio of the auxiliary metal to the carrier is (1-40):100.

10. The catalyst according to claim 8, wherein the auxiliary metal is copper, and the mass ratio of the auxiliary metal to the carrier is (0.5-15):100.

11. The catalyst according to claim 8, wherein the auxiliary metal is at least one selected from the group consisting of platinum, palladium, rhodium, iridium, silver and gold, and the mass ratio of the auxiliary metal to the carrier is (0.002-1):100.

12. The catalyst according to claim 8, wherein the auxiliary metal is at least one selected from the group consisting of magnesium, calcium, strontium, barium, sodium and potassium, and the mass ratio of the auxiliary metal to the carrier is (0.5-15):100.

13. A method for preparing the Fischer-Tropsch synthesis catalyst according to claim 1, wherein the method comprises the following steps: (1) preparing a nitride carrier having a specific surface area of not less than 80 m$^2$/g; (2) supporting a precursor of active metal as an active component and a precursor of optional auxiliary metal on the nitride carrier to form a catalyst precursor; (3) molding the catalyst precursor to obtain a molded catalyst precursor; and (4) drying and calcining the molded catalyst precursor to obtain the catalyst;

wherein the nitride carrier is a boron nitride carrier and/or a silicon nitride carrier, and wherein the active component is at least one selected from iron and cobalt.

14. The method according to claim 13, wherein the precursor of the active metal is one or more selected from the group consisting of ferric nitrate, ferric chloride, ferrous chloride, ferrous sulfate, ferrous acetate, iron(III) acetylacetonate, carbonyl iron, ferrocene, cobalt nitrate, cobalt chloride, cobalt formate, cobalt acetate, cobalt acetylacetonate, and cobalt carbonyl.

15. The method according to claim 13, wherein the precursor of the auxiliary metal is one or more selected from the group consisting of manganese nitrate, manganese chloride, manganese acetate, manganese acetylacetonate, manganese carbonyl, zinc nitrate, zinc chloride, zinc sulfate, zinc acetate, zinc acetylacetonate, chromium nitrate, chromium chloride, chromium sulfate, ammonium molybdate, platinum chloride, platinum nitrate, chloroplatinic acid, ammonium chloroplatinate, diamine platinum nitrite, rhodium nitrate, rhodium chloride, rhodium sulfate, rhodium acetate, tris(triphenylphosphine) rhodium chloride, acetylacetonatocarbonyltriphenylphosphinerhodium, palladium nitrate, palladium chloride, palladium sulfate, palladium acetate, ammonium tetrachloropalladate, ammonium hexachloropalladate, triphenylphosphine palladium, chloro-iridic acid, iridium chloride, iridium acetate, ammonium chloroiridate, gold chloride, chloroauric acid, ammonium chloroaurate, silver nitrate, silver acetate, silver carbonate, magnesium nitrate, magnesium chloride, magnesium acetate, calcium nitrate, calcium chloride, calcium acetate, strontium nitrate, strontium chloride, strontium acetate, sodium nitrate, sodium chloride, sodium acetate, sodium hydroxide, sodium carbonate, sodium bicarbonate, potassium nitrate, potassium chloride, potassium hydroxide, potassium carbonate, potassium bicarbonate, and potassium acetate.

16. A Fischer-Tropsch synthesis reaction method, comprising: preparing hydrocarbon compounds by catalyzing a syngas having volume ratio of H2:CO from 1:1 to 3:1 with the Fischer-Tropsch synthesis catalyst according to claim 1 under the pressure of 1.0 to 6.0 MPa and temperature of 150-280° C.

17. The Fischer-Tropsch synthesis reaction method according to claim 16, wherein the syngas is introduced into a Fischer-Tropsch synthesis reactor to contact with the catalyst; and the hydrocarbon compounds are prepared through carrying out a reaction by catalyzing the syngas with the catalyst.

18. The Fischer-Tropsch synthesis reaction method according to claim 16, wherein the catalyst is previously reduced in a reducing atmosphere prior to application of the catalyst to the Fischer-Tropsch synthesis reaction.

* * * * *